(12) United States Patent
Borrego et al.

(10) Patent No.: US 11,830,350 B2
(45) Date of Patent: Nov. 28, 2023

(54) METHOD AND SYSTEM FOR INSTALLING WIRELESS SOIL CONDITION DETECTION DEVICES AND MONITORING AND USING SIGNALS TRANSMITTED THEREFROM

(71) Applicant: Gravity Technologies, LLC, Mercer Island, WA (US)

(72) Inventors: Diego A. Borrego, San Diego, CA (US); Bradley A. David, San Diego, CA (US); David Adams, Seattle, WA (US); Steven Loudon, Grosse Point, MI (US); Stephen Philip Kirkpatrick, Del Mar, CA (US)

(73) Assignee: GRAVITY TECHNOLOGIES, LLC, Mercer Island, WA (US)

(*) Notice: Subject to any disclaimer, the term of this patent is extended or adjusted under 35 U.S.C. 154(b) by 287 days.

(21) Appl. No.: 17/398,414

(22) Filed: Aug. 10, 2021

(65) Prior Publication Data

US 2022/0046338 A1 Feb. 10, 2022

Related U.S. Application Data

(60) Provisional application No. 63/078,535, filed on Sep. 15, 2020, provisional application No. 63/063,909, filed on Aug. 10, 2020.

(51) Int. Cl.
*H04W 64/00* (2009.01)
*H04B 17/318* (2015.01)
(Continued)

(52) U.S. Cl.
CPC .............. *G08B 5/22* (2013.01); *E02D 1/00* (2013.01); *G01N 33/24* (2013.01); *G01S 19/13* (2013.01)

(58) Field of Classification Search
CPC .. G08B 5/22; E02D 1/00; G01N 33/24; G01S 19/13; H04B 17/318; H04B 1/005;
(Continued)

(56) References Cited

U.S. PATENT DOCUMENTS 7,483,791 B2 * 1/2009 Anderegg ............. E01C 19/288
                                                        404/117
11,035,838 B2 * 6/2021 Willness ............... G01N 27/043
(Continued)

*Primary Examiner* — Andrew Wendell
(74) *Attorney, Agent, or Firm* — DOUGHTY LAW, L.L.C.; John L. Doughty

(57) ABSTRACT

Multiple subterranean probes at an area of land detect soil conditions and wirelessly transmit soil condition information to a service provider's backend server or to a technician's hand-held wireless device. The server provides multiple user interface screens of a customer application that display soil condition information and irrigation's system status. Local micro weather stations may determine and wirelessly transmit weather condition information to the server. An installer may use the customer application to determine that received signal strength at a given probe is weak and should thus be relocated, or to determine refined location information corresponding to the probe. Historical soil condition information and artificial intelligence may predict soil conditions where a previously installed probe has been moved or quit working. Probes' housings seal internal electronics, including soil condition sensors, wireless communication modules, processors, and memory. Location coordinates may be acquired at a supra-high rate to increase location determination precision.

16 Claims, 16 Drawing Sheets

(51) Int. Cl.
  *G08B 5/22*   (2006.01)
  *G01N 33/24*  (2006.01)
  *E02D 1/00*   (2006.01)
  *G01S 19/13*  (2010.01)

(58) Field of Classification Search
  CPC ........ H04B 1/38; H04W 64/003; H04W 4/02;
        H04W 4/029; H04Q 2209/40; H04Q 9/00
  See application file for complete search history.

(56) References Cited

U.S. PATENT DOCUMENTS

| | | | |
|---|---|---|---|
| 11,212,968 B2* | 1/2022 | Hung | A01G 9/0299 |
| 2015/0096368 A1* | 4/2015 | O'Brien | E02D 1/00 |
| | | | 73/32 R |
| 2017/0023541 A1* | 1/2017 | Ellegaard | H04Q 9/04 |
| 2017/0241973 A1* | 8/2017 | Chan | H04Q 9/00 |
| 2019/0150357 A1* | 5/2019 | Wu | H04N 7/188 |
| 2020/0116894 A1* | 4/2020 | Sale | G01V 11/00 |
| 2020/0117783 A1* | 4/2020 | Apostolos | G06V 40/1376 |
| 2020/0146226 A1* | 5/2020 | Hamilton | G06Q 10/0631 |
| 2021/0215595 A1* | 7/2021 | Henry | G01N 21/31 |
| 2023/0059998 A1* | 2/2023 | Murray | G01N 27/223 |

* cited by examiner

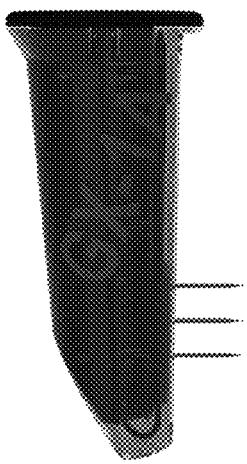
FIG. 9

The Lid (Injection Molded): The GX-1A Sensor has a lid that is attached with machine screws to the top of the outer casing. The top is slightly rounded and has an engraved GroundWorx logo.

Main Body - Exterior Capsule (Injection Molded) with Measuring Markings: The flat front design on the external capsule allows for engraved measurement markings with inches on the right side and centimeters on the left side. Measurement start at 1" from the very top of the lid, on down. (Design dimension is 9" in length).

Injection Molding Notes: The main capsule is made up of a single molded piece; one side with a slot for sensor slide functionality and the rest of the capsule allows for a hermetically sealed chamber for the electronics and battery components. (Includes a "flat area" on the capsule for an activation reed switch magnet to be attached in proximity to the PCB board for activation and provisioning.)

Sensor Measurement Range: The sensor measurements start at 1" from top of the unit and go to a depth of 9" when sensor is at ground level. Depending on connectivity, each sensor may be completely buried to various depth.

Internal Waterproof Enclosure: Withing the capsule is a two-piece waterproof enclosure that houses the proprietary PCB circuit board and battery pack. Eight machine screws with gaskets ensure the chamber is sealed and waterproof.

Bottom Design: The bottom of the sensor is designed to allow for an anchor-like pivot insertion into the root base. The back, slanted area will have dirt under it and will act as a shock absorber when carts or people contact the sensor while it sits at ground level.

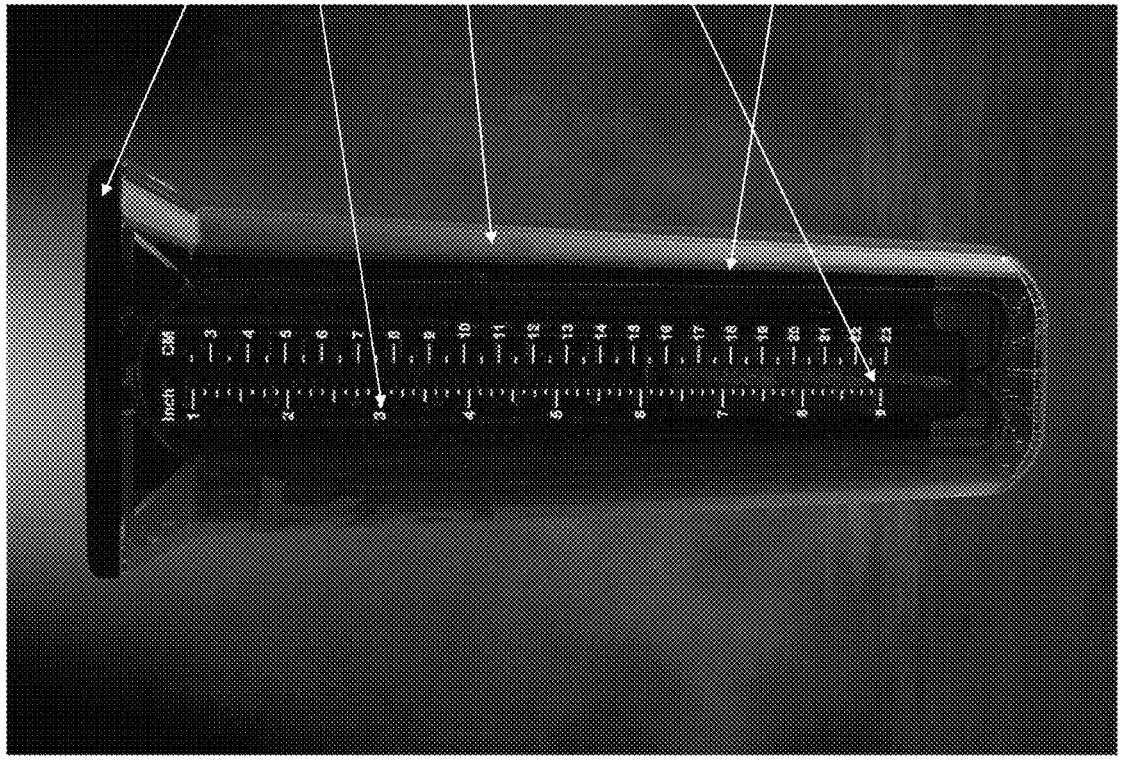

FIG. 15

METHOD AND SYSTEM FOR INSTALLING WIRELESS SOIL CONDITION DETECTION DEVICES AND MONITORING AND USING SIGNALS TRANSMITTED THEREFROM

CROSS REFERENCE TO RELATED APPLICATION

This application claims priority under 35 U.S.C. 119(e) to U.S. provisional patent application No. 63/063,909 "Method and system for monitoring and providing irrigation," which was filed Aug. 10, 2020, and which is incorporated herein by reference in its entirety, and this application also claims priority under 35 U.S.C. 119(e) to U.S. provisional patent application No. 63/078,535 "Method and system for installing wireless soil condition detection devices and monitoring and using signals transmitted therefrom," which was filed Sep. 15, 2020, and which is also incorporated herein by reference in its entirety.

FIELD

The field relates, generally, to installing wireless soil condition detection devices and monitoring wireless signals received therefrom to reduce usage of water, fertilizer, and other chemicals in a landscape such as a golf course.

BACKGROUND

To monitor moisture, salinity, PH level, or other parameters in a landscape environment, such as a golf course, systems have been used that include multiple soil condition probe devices buried at various locations at a golf course or other turf. Soil condition probes are typically connected by wires that are also buried underneath the ground (i.e., subterranean) like the probes. The wires provide communication and in some cases power to the probes from a central monitoring station device. From time to time it may be desirable to move one or more soil condition probes to different locations at a given golf course, or perhaps even to a different golf course. This presents a problem as the communication and power wires are buried under the ground. Moving a given probe from one location to another, or adding a new probe to another location, is problematic because it requires digging up the golf course.

SUMMARY

In an aspect, soil condition probes are manufactured with wireless communication modules to facilitate transmitting and receiving information via a long-range wireless communication network, such as for example, a cellular data network. Examples of such wireless data networks includes CDMA, GSM, LTE, EPC, 3G, 4G, 5G, and the like, as may be provided by mobile network operator service providers ("MNO") such as AT&T, Verizon, Sprint, and T-Mobile. The wireless soil condition detection probes include batteries. Thus, a given soil condition detection probe may be buried subterranean at a golf course without having dig up more ground than is necessary to bury the probe itself—no digging to bury communication or power wires is required.

In an aspect, local weather stations (i.e., local to a given golf course or other landscape environment) may be used to supplement, or supplant, weather reports received from a third-party internet weather service provider. A given golf course may use one or more such a local weather stations to wirelessly provide weather conditions corresponding to a particular hole of the golf course to a central monitoring station that also is configured to receive and process information and data transmitted wirelessly from one or more of the wireless soil condition detection probes. The central monitoring station, which may be connected to a communication network, such as the Internet, may receive information wirelessly transmitted from the local weather stations and the wireless soil detection probe devices from a mobile network operator's packet core network corresponding to a radio access Network with which the packet core network is associated.

In an aspect, a wireless soil condition probe device includes a long-range wireless transceiver module, that itself includes a processor, for processing data and for transmitting and received data with a mobile network operator's wireless communication network. A wireless soil condition probe may also include multi-station wireless location system circuitry, such as for example, Global Position Satellite ("GPS") circuitry, to determine the location of the soil condition detection probe in which it is installed. In an alternative embodiment, instead of using GPS radio circuitry, a given wireless soil condition detection probe may use triangulation techniques based on receiving multiple signals from multiple transmit towers of an MNO's wireless network. A wireless soil condition detection probe may also include a wake-timer/processor, which typically consumes much less power than the processor of the long-range wireless transceiver module. The transceiver module and the wake timer are typically coupled with a memory that is included in the probe. The memory may be a discrete component or may be part of the long-range wireless transceiver module. The transceiver module, the wake timer, the memory, and the GPS circuitry receive power from a battery that is enclosed with in the probes water-sealed housing. One or more sensors provide soil condition signals to the wireless transceiver module. For example, a detection probe device may include a volumetric water content sensor and corresponding detection probe, a soil dielectric sensor and corresponding detection probe, a temperature sensor and corresponding detection probe, and a bulk electric conductivity sensor and corresponding detection probe. From these sensors and corresponding probes, values and other information corresponding to other parameters may be derived, for example, P.H. or salinity. A given wireless soil detection probe device may also include one or more accelerometers that may be used to detect motion, or lack thereof, of the probe device.

In an aspect a method for installing a wireless soil condition detection/monitoring device in a subterranean location comprises activating a wireless transceiver of the soil condition/monitor device. The soil condition detection/ monitoring device includes a processor to: receive signals from one or more soil condition parameter detection sensors; cause the transceiver to wirelessly transmit and receive information corresponding to the signals received from the one or more soil condition parameter detection sensor. The transceiver may be configured to communicate wirelessly with a long-range wireless communication network. This provides an advantage that wires, conductors, or light fibers are not used to connect discrete sol condition detection devices to each other or to a central monitoring station.

At a first subterranean location, which location may be above the surface of ground where a hole has been dug or may be dug in the future depending on signal strength values as discussed in more detail herein, below the surface of ground in a hole that has been dug as determined by signal strength values as described elsewhere herein, or may be resting on top of ground where a hole may not have been dug yet but may be dug as determined by signal strength values as described elsewhere herein, that corresponds to one of the discrete soil condition detection devices/units the method includes monitoring at one or more times the strength of wireless radio signals received by the transceiver from the long-range wireless communication network.

The method may include processing over a predetermined period, or for a predetermined number of samples, the value, or values, corresponding to the strength of wireless radio signals received by the transceiver from the long-range wireless communication network to determine a processed received signal strength value. One or more values representing the strength of a signal, or signals, received at the transceiver may be wirelessly transmitted to a local user equipment device ("UE") such as, for example, an installer's smart phone or wireless tablet, via a short range wireless communication link such as Bluetooth. Or, a value representing the signal strength may be transmitted via a long range wireless cellular data link to a central monitoring station (i.e., an internet-connected computer) or back to the local installer's UE via a long range wireless internet data link.

An installer's UE or another internet-connection computer, may compare the processed received signal strength to a predetermined signal strength criterion and determine whether the processed received signal strength meets the predetermined signal strength criterion. The installers UE or the central monitoring computer may alert an installer whether or not to install the soil condition monitor device at the first subterranean location based on the comparing of the processed received signal strength value to the predetermined signal strength criterion.

In an aspect, the activating of the wireless transceiver includes may cause switch contacts of a switch having a component external to the soil condition monitoring device to complete a circuit to thereby provide electrical power to the transceiver. The component may be a switch, or a mechanical component of a switch that is part of, and external to, a housing of the soil condition detection device. The mechanical component may be an arm, lever, or the like, that penetrates the housing of the soil condition detection device to operate contacts that are contained within the soil condition detection device. Preferable, an arm, level, button, slide button, knob, or like mechanisms includes a magnet that is configured to move from a 'shipping' position to an 'activated' position. The mechanism may be biased toward the activated position. A biasing force may be provided by a spring, gravity, or other similar means. When biased and in the shipping position, the switch component may be held away from the activated position by tape, a pin, a snap, a detent, or other similar means. An installer may remove the restraining mechanism (i.e., adhesive tape) such that the mechanical component moves the magnet toward the activated position. Or, an installer of the soil condition detection device may overcome a detent preload and slide a button that is attached to a magnet from the shipping position to the activated position. When the magnet is moved from its shipping position to the activated position, magnetic field/flux from the magnet causes contents of a reed switch that is internal to the soil condition detection device to make up, thus completing a circuit within the soil condition detection device. The contacts complete a circuitry from a battery of the soil condition detection device, thus providing electrical power to the transceiver and to other circuitry components of the soil condition detection device.

As discussed, component external to the soil condition monitoring device may be part of a reed switch system; wherein the component external to the soil condition monitoring device includes a magnetic portion, wherein the component external to the soil condition monitoring device is temporarily held in a position such that the contacts do not provide a completed circuit to provide power to the transceiver, and wherein the causing of the switch contacts to complete the circuit to thereby provide electrical power to the transceiver includes removing an adhesive-coated tape such that a bias of the component external to the device moves the component in a direction of at least one of the contacts. By using a reed switch internal to the soil condition detection device with contacts that are operated, or 'made up,' by a component external to the soil condition detection device, an 'on/off' switch that physically penetrates the housing of the soil condition detection device is not required, thus eliminating a moisture pathway from subterranean soil in which the soil condition detection device is buried to the internals thereof.

In an aspect, the predetermined signal strength criterion is based on a signal strength attenuation value that corresponds to a type of soil that will cover the soil condition monitor device at the first subterranean location.

In an aspect, the installer is alerted not to install the soil condition detection at the first subterranean location when the processed received signal strength does not meet the predetermined signal strength criterion. The alert may be received by a UE being used by the installer, by a handheld wireless device that is configured specifically to communicate with soil condition detection devices or that is configured to communication with a central monitoring station computer that itself is configured to wirelessly communicate with soil condition detection devices.

In an aspect the predetermined signal strength criterion is based on a signal strength attenuation value that corresponds to a type of soil that will cover the soil condition monitor device at the first subterranean location and on a predetermined depth at which the device is to be buried. For example, if the soil condition detection device is to be buried in under a first turf species with a root base of a first depth that is deeper than a second depth that may correspond to a different second species of turf, the signal strength criterion may be a higher value than if the soil condition detection device were to be buried at the second depth under the second turf species. In other words, a higher signal strength criterion value would require a stronger processed signal strength value to avoid the installer being alerted that the location for burial of the soil condition detection device is not satisfactory because adequate signal strength for wireless communion with a long-range wireless network does not exist. For turf species with shallower root bases than the first species the signal strength criterion value could be lower and thus weaker signals might still not alert an installer that the location where the soil condition detection device is to be buried is not acceptable.

In an aspect, when an installer is alerted that the signal strength of communication signals received from the long range wireless communication will be inadequate to support wireless communication between the long range wireless network and a transceiver of the soil condition detection device when the device is buried below the root base of the turf species at the given first location, one or more of the steps described above may be performed for a second subterranean location when the processed received signal strength at the first location does not meet the predetermined signal strength criterion.

In an aspect, a method for refining the precision of the determining of location information of a soil condition detection device at a first location provided by a multi-station wireless location determining system, that in an aspect, for example, is a Global Positioning Satellite ("GPS") system, or for another example is a multi-station cellular radio network having multiple stations within signal range of the soil condition detection device, comprises capturing first location information based on transmission signals from the multi-station wireless location system (i.e., GPS signals) at the first location at a first sample rate. The capturing may include the generating by a GPS receiver of the soil condition detection device location coordinates. The capturing may also include receiving the location coordinates by a processor of the soil condition detection device, for example, the processor of a transceiver module of the soil condition detection device.

A determination may be made that the soil condition detection device has not moved from the first location during a predetermined first period. The determination may be made by a processor that is part of a transceiver of the soil condition detection device. The determination may be made by a remote/central monitoring station that monitors signals transmitted from the soil condition detection device. Or, an installers UE may make the determination. The determination may be made by processing signals that may be generated by accelerometers of the soil condition detection device during the predetermined first period. The determination may be made by processing signals or information that GPS circuitry of the soil condition detection device may generate during the predetermined first period. The predetermined first period may be any period, but in an aspect may be selected in software (typically running on the processor of the transceiver of the soil condition detection device) as a period of ten seconds.

Whatever device, processor, or station computer makes the determination that the soil condition detection device has not moved, may store location information corresponding to a sample captured at the first sample rate as indicating the location of the soil condition detection device. The device, processor, or station computer may capture location information based on transmission signals from the multi-station wireless location system at a second sample rate at the first location for a second plurality of samples during a predetermined second period. The predetermined second period typically occurs after the predetermined first period.

After the second plurality of samples have been captured and stored, a centroid is determined of data points corresponding to the second plurality of samples captured while the soil condition detection device is at the first location. Information corresponding to the sample captured at the first sample rate is replaced with the centroid corresponding to the second plurality of samples as indicating the location of the soil condition detection device. The second sample rate is preferably higher than the first sample rate. This provides the advantage that multiple location coordinate sets provide a more precise determination of location coordinates, and by sampling GPS data, or location information from another source, at a higher sample rate than the first sample rate speeds up the installation process of the given soil condition detection device.

In an aspect, the device, processor, or monitoring computer that performs the determination of the centroid may determine, after the replacing of the information corresponding to the sample captured at the first sample rate with the centroid location coordinate set corresponding to the second plurality of samples the location of the soil condition monitor device, second location information as corresponding to the location of the soil condition monitor device at the first sample rate. A determination may then be made that the soil condition monitor device has been moved from the first location based on a comparison between the centroid corresponding to the second plurality of samples and the second location information, and a notification may be provided to a service provider's backend server that the soil condition monitor device has moved from the first location when the comparison between the centroid and the second location information indicates a difference that is greater than a predetermined location difference value.

In an alternative aspect, instead of determining a second location at a first sample rate using GPS circuitry, the transceiver may be awakened by, or triggered by, a signal generated by an accelerometer of the soil condition detection device. The signal received from the accelerometer may be evaluated to determine whether the signal represents seismic activity, such as earthquake or volcanic activity. If not, the transceiver my instruct GPS circuitry to boot up/wake up and determine the location of the soil condition detection device, and whether the device has moved from the first location. Evaluating accelerometer signal information and determining that the information corresponds to seismic activity, nearby heavy machinery activity, or even a powerful thunderclap, provides the advantage of not powering up GPS circuitry when the likelihood is low that the accelerometer signal was generated by the moving of the location of the soil condition detection device.

In an aspect, the predetermined location difference value is based on the precision in determining location information that is obtainable from signals of the multi-station wireless location system sampled at the first sample rate. For example, if the best precision that a GPS receiver can provide at a sample rate of 10 Hz is 25 feet, the predetermined location difference value would be selected to be greater than 25 feet. Otherwise, if the predetermined location difference value were selected to be less than 25 feet, then one or more spurious location coordinate determinations from a soil condition detection device's GPS circuitry could indicate that the soil condition detection device had been moved which it in fact had not been moved. In an aspect, if an accelerometer signal indicates that a given soil condition detection device has experienced movement, GPS circuitry of soil condition detection device may obtain samples at the higher second sample rate as discussed above to compare with the second location information as corresponding to the location of the soil condition monitor device at the second, higher sample rate.

In an aspect, the sample rates are sentence rates.

In an aspect, a method comprises receiving soil condition information transmitted wirelessly from each of a plurality of subterranean soil condition detection devices buried at corresponding original locations within an area of land during a first period. The soil condition information corresponding to each of the plurality of subterranean soil condition detection devices received during the first period is stored in a customer location table. One of the plurality of subterranean soil condition detection devices to be moved from its corresponding original location is identified as being a device to be moved. A device may be so identified when, for example, one device is buried close to another devices and over time soil conditions at the locations of both devices is reported as being the same or almost the same. Or, a device may be identified for moving to another location if signal strength at the original subterranean location of the device has been poor over a period of time, such as a week or a month.

After being identified for movement, the identified one of the plurality of subterranean soil condition detection devices is moved from its corresponding original location to a new location within the area of land. During a second period, soil condition information that is transmitted wirelessly from each of the plurality of subterranean soil condition detection devices buried at corresponding locations within an area of land is received, including information from the identified one of the plurality of subterranean soil condition detection devices that is now buried at its new location within the area of land.

A determination of soil conditions at the original location of the identified one of the plurality of subterranean soil condition detection devices that was moved from its original location to its new location may be made based on soil condition information received during the first period from at least one of the plurality of subterranean soil condition detection devices other than the identified subterranean soil condition detection device that was moved and based on soil condition information received during the second period from the at least one of the plurality of subterranean soil condition detection devices other than the identified subterranean soil condition detection device that was moved.

In other words, over a period, which may be referred to as a learning period, or a training period, data corresponding to soil condition information corresponding to the soil condition detection devices that said devices transmitted from their original locations is stored. After the soil condition information obtained during the training period is stored, information from any of the soil condition detection devices may be used to calculate, or determine, the soil conditions at the location of a given other of the soil condition detection devices even if the given other device is not functioning. Or, instead of determining the soil conditions of a soil condition detection devices that is not functioning, soil condition information obtained during the training period may be used to determine soil conditions at a time after the training period at the original location of one of the soil condition detection devices that has been moved from its original location. Thus, a greenskeeper, or landscape manager, may build a database over time of soil conditions information corresponding to a plurality of soil condition detection devices and continue to determine soil conditions at the original locations of soil condition detection devices that have been moved to new locations.

In an aspect, the determining of the soil conditions at the original location of the identified one of the plurality of subterranean soil condition detection devices that was moved from its original location to its new location includes processing with an artificial intelligence algorithm the soil condition information corresponding to each of the plurality of subterranean soil condition detection devices received during the first period, or training period, to determine an original location model corresponding to the location of the soil condition detection device that was moved, and applying the original location model to the soil condition information transmitted wirelessly from each of the plurality of subterranean soil condition detection devices during the second period, (i.e, at a time, or times, after the training period), except that information corresponding to the device that was moved to a new location, may not be used to estimate the soil conditions at the original location of the device that was moved during the second period.

In an aspect, the original location model is determined using a supervised regression algorithm.

In an aspect, the determining of the soil condition at the original location of the identified one of the plurality of subterranean soil condition detection devices that was moved from its original location to its new location includes processing with a neural network the soil condition information corresponding to each of the plurality of subterranean soil condition detection devices received during the first period to determine an original location model corresponding to the location of the soil condition detection device that was moved, and applying the original location model to the soil condition information transmitted wirelessly from each of the plurality of subterranean soil condition detection devices during the second period, except for the device that was moved to a new location, to estimate the soil conditions at the original location of the device that was moved during the second period.

BRIEF DESCRIPTION OF DRAWINGS

FIGS. 9, 10, and 11 illustrate an installer interface of a customer application that indicates a predetermined depth to bury a soil condition detection probe device based on signal strength as a desired location to place a subterranean probe device.

FIG. 15 illustrates a illustrates a side view of an outside housing of a soil condition detection device that describes features of the soil condition detection device.

DETAILED DESCRIPTION

As a preliminary matter, it will be readily understood by those persons skilled in the art that the present invention is susceptible of broad utility and application. Many methods, embodiments, and adaptations of the present invention other than those herein described as well as many variations, modifications and equivalent arrangements, will be apparent from or reasonably suggested by the substance or scope of the present invention.

Accordingly, while the present invention has been described herein in detail in relation to preferred embodiments, it is to be understood that this disclosure is only illustrative and exemplary of the present invention and is made merely for the purposes of providing a full and enabling disclosure of the invention. The following disclosure is not intended nor is to be construed to limit the present invention or otherwise exclude any such other embodiments, adaptations, variations, modifications and equivalent arrangements, the present invention being limited only by the claims appended hereto and the equivalents thereof.

Figure 1:
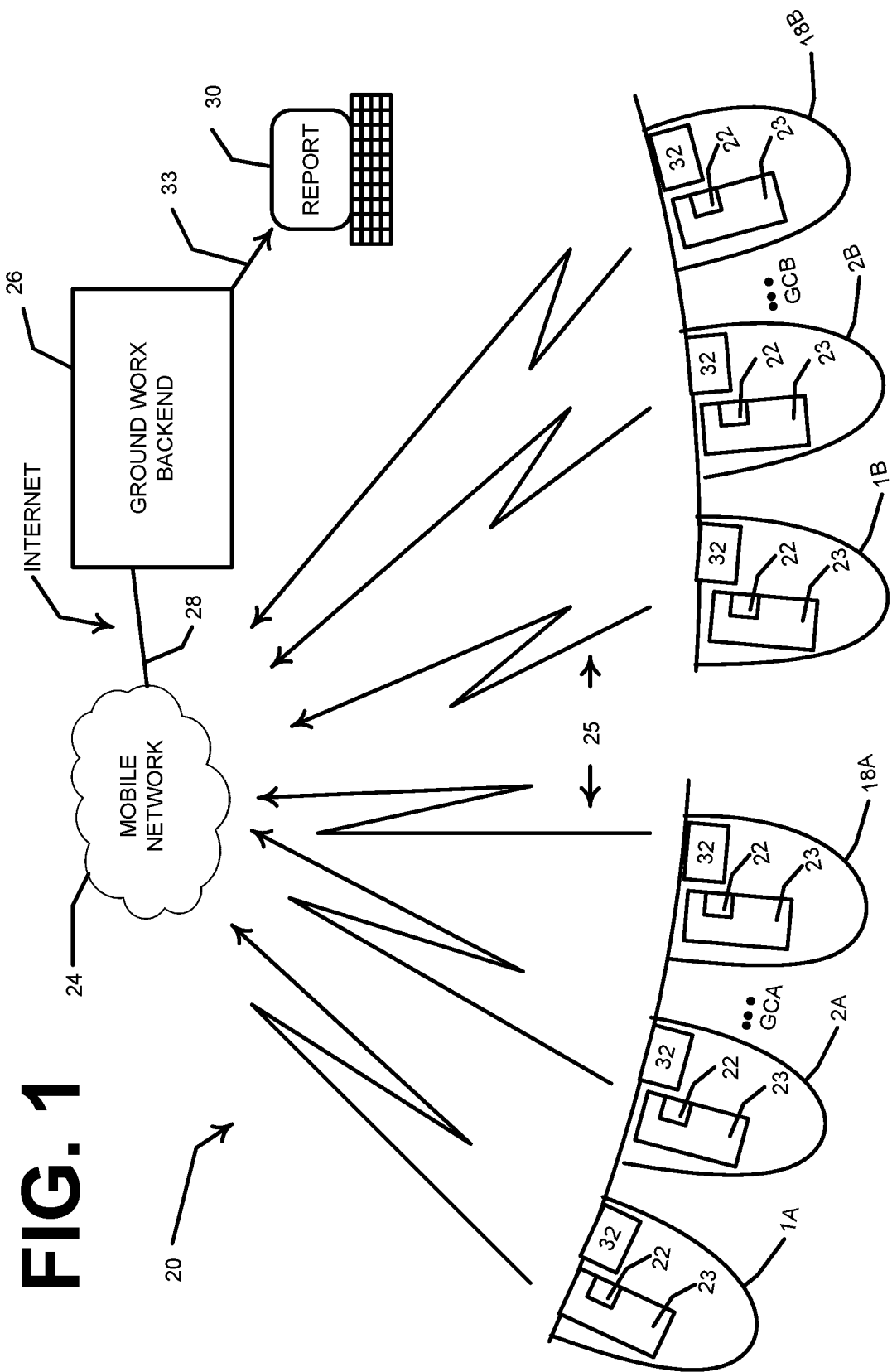
FIG. 1 illustrates a plurality of golf courses with a plurality of wireless soil condition detection devices at each golf course.

Turning now to the figures, FIG. 1 illustrates a landscape environment 20 having a plurality of golf courses A and B. It will be appreciated that aspects described herein may apply to more than two golf courses, but two courses A and B are shown for purposes of clarity. Each golf course typically has eighteen holes, as represented by areas 1A, 2A, ... 18A with respect to golf course A and by areas 1B, 2B, ... 18B with respect to golf course B. Each hole area typically includes at least one soil condition detection probe device 22 buried in corresponding probe hole 23. Each probe device 22 includes a wireless transceiver circuit that can communicate with mobile network 24 via long-range wireless signal links 25. Mobile network 24 is coupled to a central monitoring computer station/server/system backend 26 via communication link 28. Connection 28 may be wired or wireless and may be an internet link or link of a similar type of communication network. Backend server 26 communicates with a user device 30, such as a desktop computer, a lap top computer, a tablet, a notebook, a smart phone, and the like, via communication link 33. Communication link 33 may be wired or wireless and may be an internet link or link of a similar type of communication network. Environment 20 is shown with an irrigation/sprinkler head 32 at each of the golf course hole areas. It will be appreciated that more than one irrigation head may be installed subterranean at each hole area, or a given hole area may be served by no irrigation heads.

Figure 2:
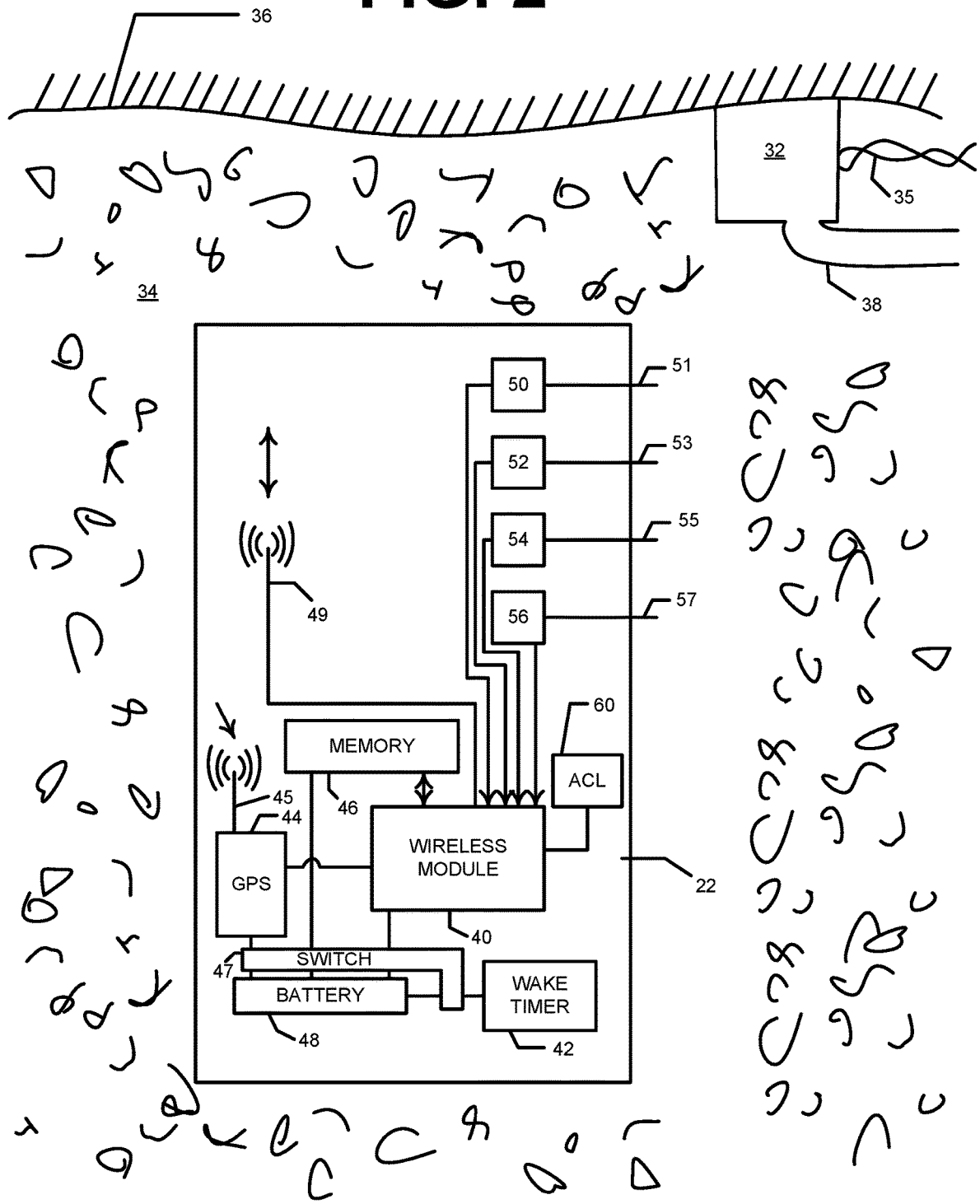
FIG. 2 illustrates block diagram of a soil detection device buried in the ground.

Turning now to FIG. 2, the figure illustrates a soil condition detection probe device 22 buried subterranean in ground 34 beneath the ground's surface 36. Surface 36 is shown with grass as may be typical at landscaping installations such as golf courses. Sprinkler/irrigation head 32 is shown with supply pipe 38 that supplies water to the sprinkler and power wires 35 that energize the sprinkler head when an irrigation system control device causes such power to be provided in response to a control signal generated by a computer device, such as, for examples, user device 30 and/or backend server 26 shown in FIG. 1. User device 30 and/or backend server 26 may generate/modify said control signal, or signals, based on evaluation of information contained in signals that correspond to soil condition(s) detected by sensors of, and processed and transmitted by, a wireless transceiver of soil condition detection probe device 22. Control signals to operate irrigation head(s) 32 may be based on a predetermined schedule. User device 30 and/or backend server 26 may override a predetermined irrigation schedule based on the evaluation of soil conditions by one or more soil condition detection device(s) 22 that correspond(s), or that correspond respectively, to an area, or areas, of land that can be irrigated by irrigation heads(s) 32. User device 30 and/or backend server 26 may generate/modify control signals based on manual input from a user who may determine that a given area of land needs to be watered based on evaluation of soil conditions by one or more soil condition detection device(s) 22 that correspond(s), or that correspond respectively, to an area, or areas, of land that can be irrigated by irrigation heads(s) 32. User device 30 and/or backend server 26 may generate/modify control signals based on automatic (i.e., without human intervention) evaluation of soil conditions by one or more soil condition detection device(s) 22 that correspond(s), or that correspond respectively, to an area, or areas, of land that can be irrigated by irrigation heads(s) 32. User device 30 and/or backend server 26 may generate/modify control signals based on signals transmitted from one or more wirelessly connected (i.e., connected to the Internet via wireless communication links) local weather stations that correspond(s), or that correspond respectively, to an area, or areas, of land that can be irrigated by irrigation heads(s) 32.

Continuing with description of FIG. 2, soil condition detection probe device 22 includes Wireless transceiver module 40, wake timer/processor 42, GPS radio circuitry 44, in memory portion 46, in the battery 48. Battery 48 provides power to transceiver module 40, wait timer processor 42, GPS radio circuitry 44, and memory portion 46. In an aspect, power from battery 48 may be provided through reed switch 47, one or more internal contacts of which may be controlled by a magnet. Tape may retain a movable components, such as an arm, lever, blade, or other similar component, which may include a magnet, in an open position such that contacts of reed switch 47 are not closed, or 'made up,' until the tape is removed by an installer and the magnet moves into a position that causes contacts of the reed switch to close, or 'make up,' thus allowing power to flow from battery 48 to other components, such as wireless communication module/processor 40, wake timer 42, GPS module 44, and memory 46 as shown in the figure. A processor of wireless transceiver module 40, which may be referred to herein as a wireless modem, communicates with GPS radio 44 wake timer 42, memory 46, and accelerometer 60. Wake timer 42 typically is a low performance/low capability processor as compared to the processor of module 40 but may stay on when the processor of module 40 is turned off for power saving purposes. Wait timer 42 may be programmed to awaken wireless module 40 according to a predetermined schedule to provide various types of communication wirelessly through antenna 49. GPS circuitry 44 communications (typically only receives) information signals from a plurality of satellites via antenna 45.

Probe device 22 includes a plurality sensors and corresponding probes that obtain soil condition information. It will be appreciated that device 22 is hermetically sealed to protect the internal components of the device from environmental factors such as moisture and temperature. Sensor 50 may be a volumetric water content sensor, sensor 52 may be a dielectric sensor, sensor 54 may be a temperature sensor, and sensors 56 may be a bulk electric conductivity sensor. Probes 51, 53, 55, and 57, correspond to sensors 50, 52, 54, and 56, respectively. Probes 51, 53, 55, and 57 may appear as metallic fingers that project from a housing of probe device 22, but the probes may differ from one another depending on the parameter that the corresponding sensor if designed to detect. Probes 51, 53, 55, and 57 project through the housing of device 22, and are sealed to prevent moisture intrusion into device 22. GPS radio circuitry 44 communicates location information (i.e., location of device 22) to a processor of transceiver module 40 and sensors 50, 52, 54, and 56 communicate detected soil information according to their parameter types to the processor of the transceiver module 40, which wirelessly transmits such location and soil information via antenna 49 through ground 34 to a central monitoring station, such as backend server 26 shown in FIG. 1.

Figure 3A:
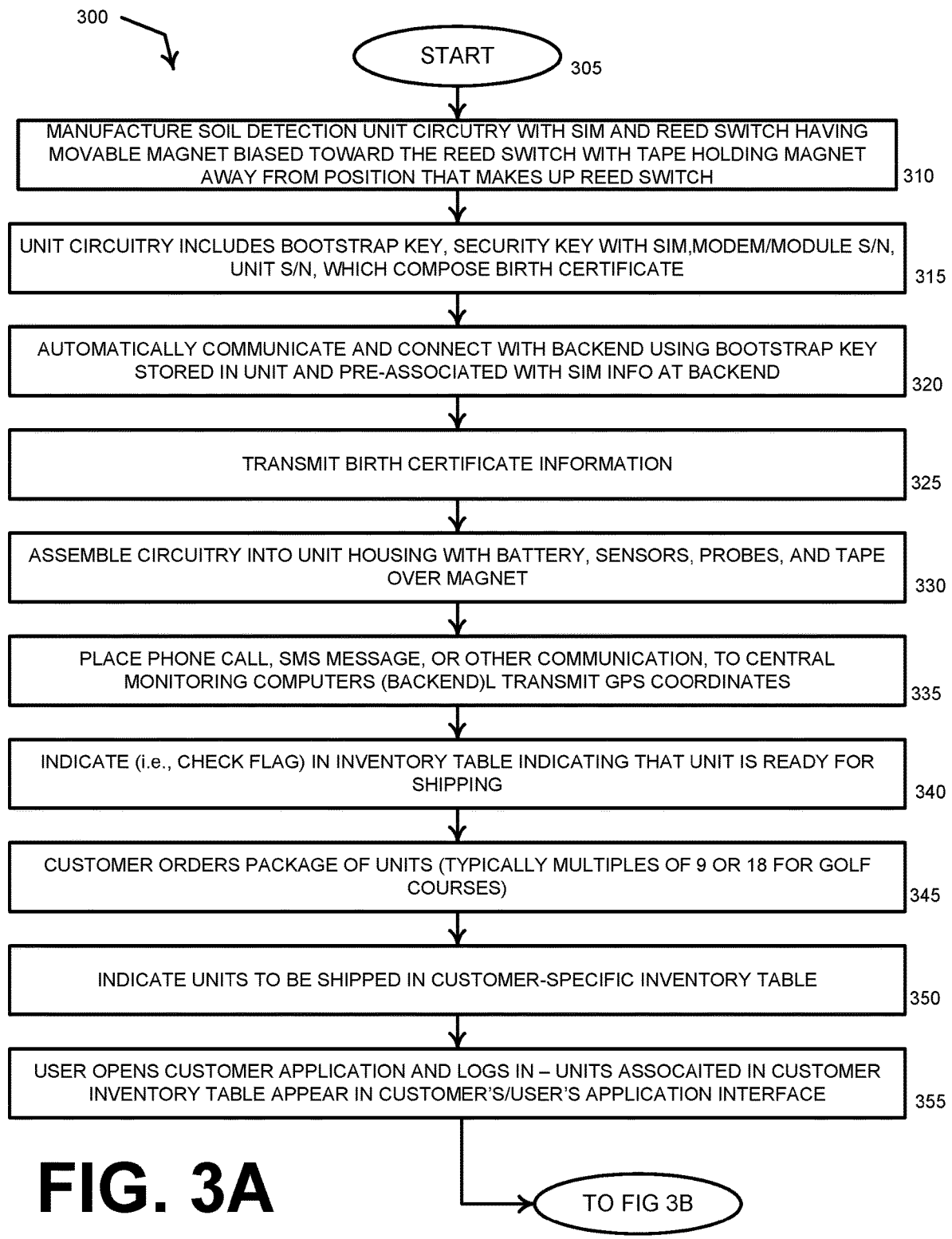
FIGS. 3A-3B illustrate a flow diagram of a method for manufacturing, provisioning, and installing one or more soil condition detection probe devices in subterranean locations.
Figure 3B:
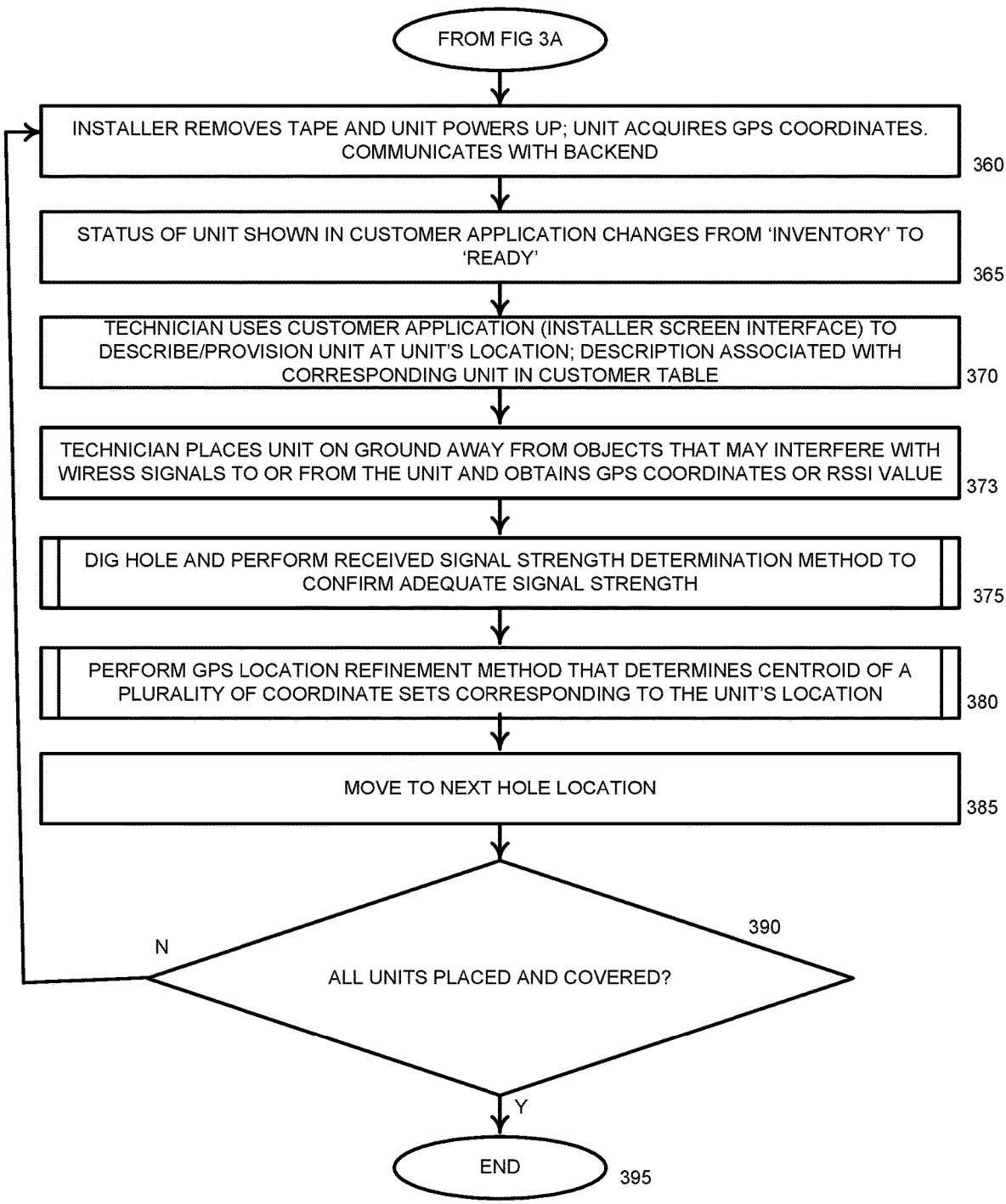

Turning now to FIG. 3, the figure illustrates a flow diagram of a method for manufacturing, provisioning, and installing one or more soil condition detection probe devices in subterranean locations. Method 300 begins at step 305. At step 310 soil condition detection probe device units are manufactured with circuitry that includes a Reed switch with a movable magnet biased in a direction that causes the magnet to cause switch contacts to make up when the magnet is moved in the biased direction. The magnet is held away from the switch contacts against the magnetic bias with a temporary restraining mechanism, such as, for example, tape. The device is also manufactured with a Subscriber Identity Module ("SIM"), which may be a SIM card or other means for storing SIM information that a conventional SIM card would include, such as unique (to the SIM) identifiers and unique (to the SIM) cryptographic information that facilitates authentication to a long-range wireless network.

At step 315 the flow diagram shows that manufactured soil condition detection device includes circuitry that includes a bootstrap key. The bootstrap key is securely associated with the SIM in a memory that is in communication with a wireless modem/transceiver module of the device as well as being associated with a serial number of the device. The memory of the device includes the bootstrap key, a serial number of the modem/transceiver, and a unit/device serial number. The bootstrap key, the modem serial number, and the device serial number together may be referred to as a 'birth certificate' or 'birth certificate information' and separately as birth certificate information. The memory that stores such information may be a memory that is part of the SIM, may be memory that is part of the modem/transceiver processor module, or may be a discrete memory that is coupled to the transceiver module and SIM.

At step 320, during the manufacturing process, power is applied to the circuitry that includes the long-range wireless module/modem/processor. The transceiver module boots up, transmits the bootstrap key to a services provider's back-end server, which uses the bootstrap key to authenticate the devices circuitry with the services provider's back-end computer server.

At step 325, the long-range wireless transceiver transmits the birth certificate to the backend server, which then associates therein separate birth certificate information components with one another.

At step 330 the soil detection device/unit is assembled by installing the device circuitry into a housing along with one or more batteries, sensors, and probes, with tape over the magnet to prevent further use of the soil detection unit until it is ready to be placed into subterranean service by an end user, such as a groundskeeper technician, and landscape technician, or the like.

At step 335, GPS circuitry, that may be part of the device circuit, or may installed as a separate circuit board than the long-range transceiver module, determines a geographic location coordinate, or coordinates, of itself (which location corresponds to the location of the device into which it has been installed), and the determined location is transmitted to the services provider's back-end server. It will be appreciated that the taping of the magnet away from the reed switch contacts, which was described above in reference to step 330, may occur after the transmitting of the device's location coordinates as described in reference to step 335.

Continuing with discussion of step 335, when the service's provider's backend server receives the device's location coordinates, the back end server identifies the device (according to the SIM's identifier/serial number, the device's serial number, or the bootstrap key's serial number) in a table/database maintained at the back end server that the device from which the location coordinates were transmitted is deemed in inventory and ready to ship from the manufacturer, or current storage location at step 340.

At step 345, a customer, for example a golf course, orders a soil detection equipment package. A typical soil detection equipment package may include a plurality of subterranean soil detection devices (typically sold in multiples of nine or eighteen, since golf courses typically have nine or eighteen holes) and optionally one or more weather station devices that may be placed at the landscape/golf course to obtain very precise micro weather information that may be more accurate for the given landscape location than commercial or government weather information feed that may be more of a macro forecast for a much larger area than the given landscape/golf course location. The local micro location weather information may be wirelessly transmitted to, and received at, the services provider's back-end server. The plurality of wireless soil detection units, after installation, wirelessly transmit detected soil conditions to the landscape services provider's backend.

After a customer orders a soil condition detection package at step 345, at step 350 the service provider's back-end server indicates which units are to be shipped to the customer who places the order at step 345. This indicating at step 350 may include creating a customer-specific inventory table, or database, at the backend server.

At step 355, after the equipment to be shipped has been included in the customer-specific inventory table according to unique identifiers (including the micro weather station device), a user/customer launches a customer application, for example on a laptop, tablet, or smart phone and logs in to the application. The customer application indicates the actual soil condition detection units, according to serial number or other unique identifier associated with the units, that are to be shipped and that have been associated with the customer's log-in information. It will be appreciated that a micro weather station device may include similar circuitry as a soil condition detection unit 22 as described elsewhere herein except that the sensors of the weather station may differ inasmuch as the weather station device would typically include sensors that are configured to monitor weather-related parameters such as barometer, temperature, humidity, etc. instead of soil-related parameters as described elsewhere herein.

At step 360, after the shipped detection units have been delivered to a customer, an installation technician ("installer") removes a soil condition detection device from its packaging and removes the tape, or other restraining mechanism, that holds the magnet back from the reed switch thus allowing current to flow from the battery of the device to the circuitry thereof which causes the circuitry of the device to 'wake up'. After the circuitry wakes up, the GPS circuitry obtains a fix, or lock, (typically to determine that the GPS receiver is receiving signals from at least four different satellites), determines its location and transmits location coordinate information to the long-range wireless transceiver modem/processor for transmission to the services provider's backend server over a wireless mobile network. The long-range wireless transceiver/module/processor/modem transmits the location coordinates to the backend server via the wireless mobile network thus indicating that the device has been activated for installation into a subterranean position.

At step 365, a status of the soil condition detection unit that transmitted the location coordinates at step 360 changes in the customer's application from being in customer 'inventory' to being 'ready' for installation. In an aspect, the moving of a given soil condition detection unit from being indicated as being in 'inventory' to being 'ready' for installation may be based on signal strength measurement information (such as RSSI) exceeding a predetermined 'ready' threshold, or simply by virtue of the fact that an RSSI value has been calculated/determined by the long-range wireless module. GPS circuitry may still be in process of establishing location coordinates after a device is indicated as 'ready' or being installed.

At step 370 the installer uses the customer application to describe textually the location of the unit that the installer is about to bury in the ground. This process may be referred to as provisioning by the installer insofar as the location of the unit to be buried is described in plain English (or other language) that the installer, or customer administrator/manager can easily understand.

At step 373 the installer may, in an aspect, place the unit on the ground generally at the location determined at step 360. Placing the unit on the ground instead of an installer holding the unit in his, or her, hand, or instead of resting in a golf cart, for example, may provide reception of long-range wireless signals in an unobstructed or undistorted fashion. It has been learned by the inventors of subject matter disclosed herein that even holding a unit by an installer in his, or her, hand may distort, alter, or disturb, electromagnetic properties, such as capacitance, inductance, permittivity, or permeability, that could alter the reception of long-range wireless signals and thus could alter RSSI value determination or GPS reception. Placing the unit on the ground away from an installer's body may more closely mimic the reception characteristics of the unit when it is placed in a subterranean location (albeit perhaps with less signal strength attenuation due to the unit not being covered by soil or grass), or at least not alter reception characteristics such that what may be acceptable reception/transmit characteristics at the location determined at step 360 while the unit is held in an installer's hand may not provide adequate reception signal strength when the unit is placed on the ground at generally the same location, thus indicating that a different location should be sought before digging a hole to place the unit in. If an RSSI value determined with the unit resting on the ground indicates that the location likely will provide adequate long-range wireless reception according to the signal strength determination method of steps 520-545 described herein in connection with step 375 and FIG. 5, the number of holes dug to find a location that provides adequate transmit/receive characteristics or performance may be minimized. Placing the unit on the ground before performing steps 520-545 may reduce the number of holes that are dug by determining, or deeming, that a given location on the ground will likely not provide adequate long-range wireless reception and corresponding RSSI values.

If the location at which steps 520-545 were performed is deemed an acceptable location based on one or more determined long-range wireless signal strength values, at step 375 the installer digs a hole to place the soil condition detection unit into at the location deemed acceptable at step 373. To deem the location acceptable, an installer may use the customer application to cause the soil condition detection device to perform a signal strength determination method to confirm that, after burial, the long-range wireless transceiver module of the detection device is in a location with adequate long-range wireless network signal coverage to facilitate wireless transmission from the detection unit to the long-range wireless mobile network. The method of determining adequate signal strength is described in more detail in reference to FIG. 5.

Continuing with description of FIG. 3, at step 380 the installer may use the customer application to cause the soil condition detection device to perform a location coordinate refinement method. The location coordinate refinement method may facilitate precise identification, using the customer application, of a subterranean soil condition detection unit after it has been buried. This provides an advantage that minimal digging to unearth a buried subterranean device will be needed. Location coordinates that a typical GPS receiver produces may be precise enough for locating a destination along a roadway because a vehicle driver can see his, or her, desired target location even if a navigation system only provides such location within a precision of 100 feet. However, better precision than this is desired in the context of digging up a golf course when seeking to replace a soil condition detection unit that may comprise a cylindrical housing having a depth of about ten inches and a diameter of about four to five inches. A given location determination from a typical GPS receiver may be precise enough for locating a soil condition detection unit buried beneath the ground surface at a golf course, but more likely than not a given determination of coordinates determined from a GPS receive will only be accurate to within a precision that is unacceptable to a groundskeeper at a golf course. Therefore, a method for refining the precision of the determination of the coordinates of the location of a soil condition detection device before the device is buried is described in more detail in reference to FIG. 4.

Continuing with description of FIG. 3, after an installer has completed steps 375 and 380 as described above, the installer covers the buried soil condition detection unit with dirt and grass, indicates that he, or she, has done so in the customer application with respect to the just-buried device identifier/description (i.e., the description entered at step 370), and moves to a next desired location to bury another soil condition detection device at step 385.

At step 390, the customer application determines whether all of the units that were originally in customers inventory and later displayed in the customer application as being 'ready' as described in reference to step 365 have been installed as indicated by the installer as described in reference to step 385. If not all of the customer's soil condition detection units have been installed and buried, method 300 returns to step 360 and installer removes the tape from the next device to be installed and buried and the method continues as described above. If the customer application determines at step 390 that all of the customer's soil condition detection units have been installed, method 300 advances to step 395 and ends.

In an aspect, a soil condition detection device/unit may be configured with one or more SIM cards, eSIMs, soft SIMs, or SIM profiles, and the like in any combination thereof. (Any combination of the forgoing SIM cards, eSIMs, soft SIMs, or SIM profiles or the like may be referred to herein as "SIM".) In an aspect, one of the one or more SIMs may be configured to operate on a long-range wireless network of a first Mobile Network Operator ("MNO") and another of the SIMs may be configured to operate on a network of a different, or second, MNO, and yet another of the SIMs may be configured to operate on a network of yet another third MNO that is not the first or second MNO. By using more than one SIM in a stationary long-range-wireless-connected device, such as a soil condition detection device/unit, a processor of the device/unit may be configured to autonomously switch the long-range wireless network that it is connected to based on a signal strength value, such as, for example, RSSI. Unlike with many mobile wireless communication devices that may be configured to maximize time in a CONNECTED state, at least a connected state such as, for example, ECM-CONNECTED according to an LTE protocol (a mobile device may be in an ECM-CONNECTED state but an RRC-IDLE state to conserve battery power of the mobile device while NAS signaling maintains an ECM connection with networking components), a stationary device that is buried in the ground and that operates exclusively on battery power and is designed to remain functional while buried in the ground without recharging batteries for extended periods, for example multiple years, may be configured to be in an unconnected mode for a very substantial portion of the period during which it is buried. Not only may a buried, stationary device such as a soil condition detection device/unit be configured to not be connected for a substantial portion of a buried period, it may also be configure to not even stay in an idle state, such as ECM-IDLE or RRC-IDLE, for most of the buried period to further conserve battery life/battery charge.

In such a scenario where a device stays in an essentially off state, timers that may draw a very, very small amount of current (on the order of a few micro amps) may operate continuously and wake the device, and its components periodically. When the device is awakened, it may be configured so that one of its processors instructs a long-range wireless module of the soil condition detection device/unit to connect to a network of a preferred MNO first using a first SIM corresponding to the preferred MNO, but if an adequate signal strength value cannot be determined for long-range wireless communication with the preferred, or first network, the processor may be configured to autonomously instruct a long-range wireless module of the soil condition detection device/unit to attempt to use a different/second SIM to attempt to connect with a network of a second MNO to determine whether the second MNO network can provide better signal strength values, and thus better wireless connectivity with the second MNO network. Similarly, if after awakening attempts to connect with either the first SIM or second SIM do not result in adequate signal strength value determinations, a processor of the soil condition detection device/unit may instruct its long-range wireless module to attempt to use a third SIM to connect to a corresponding third MNO network in an attempt to achieve better connectivity and long-range wireless performance with the third network as compared to the performance that could have been achieved with the first or second network using the first SIM or second SIM, respectively, based on determined signal strength values corresponding to the first, second, or third MNO networks, respectively. In an aspect, the processor of the soil condition detection device/unit may base a decision of which network to attempt to autonomously connect to after waking up, using a SIM corresponding to the respective network, on criteria other than signal strength values, such as, for example, measured, or otherwise determined data rate of communication over the respective network, or simply ability to connect to the respective network using the SIM corresponding to the respective network. An advantage of this aspect enhances the ability of a long-range wireless module of a soil condition detection device/unit to obtain a reliable long-range wireless data connection with an MNO network when the soil condition detection device/unit is buried in a location that may be on the periphery/fringe/edge of respective coverage areas of the first, second, and third MNO networks. In addition, an advantage is provided inasmuch as a given MNO network that may provide adequate long-range wireless signal coverage when a device is placed on the ground in a location as described in reference to steps 373 and that is evaluated as described in reference to steps 520-545 as being a location that provides adequate long-range-wireless signal strength may not always provide adequate signal coverage when network condition differ as compared to conditions on the same network when steps 520-545 were performed before placing the soil condition detection device/unit in the ground and burying it. In other words, a network, associated with a first SIM, that is deemed to provide adequate signal strength/coverage at the location when and where a given soil condition detection device/unit is buried may not provide the same level of signal strength at the same location when the processor of the soil condition detection device/unit wakes up the unit. But another one of the MNO networks, associated with a different SIM, may provide adequate signal strength/characteristics to the soil condition detection device/unit when the processor of the soil condition detection device/unit wakes the unit up. Thus. The aspect of being able to autonomously choose which SIM to use to connect with an MNO network that corresponds to the SIM based signal strength, other network or signal characteristics, or just the ability to connect at all, enhances the ability of a long-range wireless module to connect upon wake up of the soil condition detection device/unit, thus increasing the likelihood that the unit will be able to transmit soil condition information each time it wakes up, which in turn enhances battery life because the entire unit wakes up less often when it might be unable to connection to a single network that corresponds to a SIM if that SIM were the only SIM available for use by a long-range wireless module of the soil condition detection device/unit.

Figure 4:
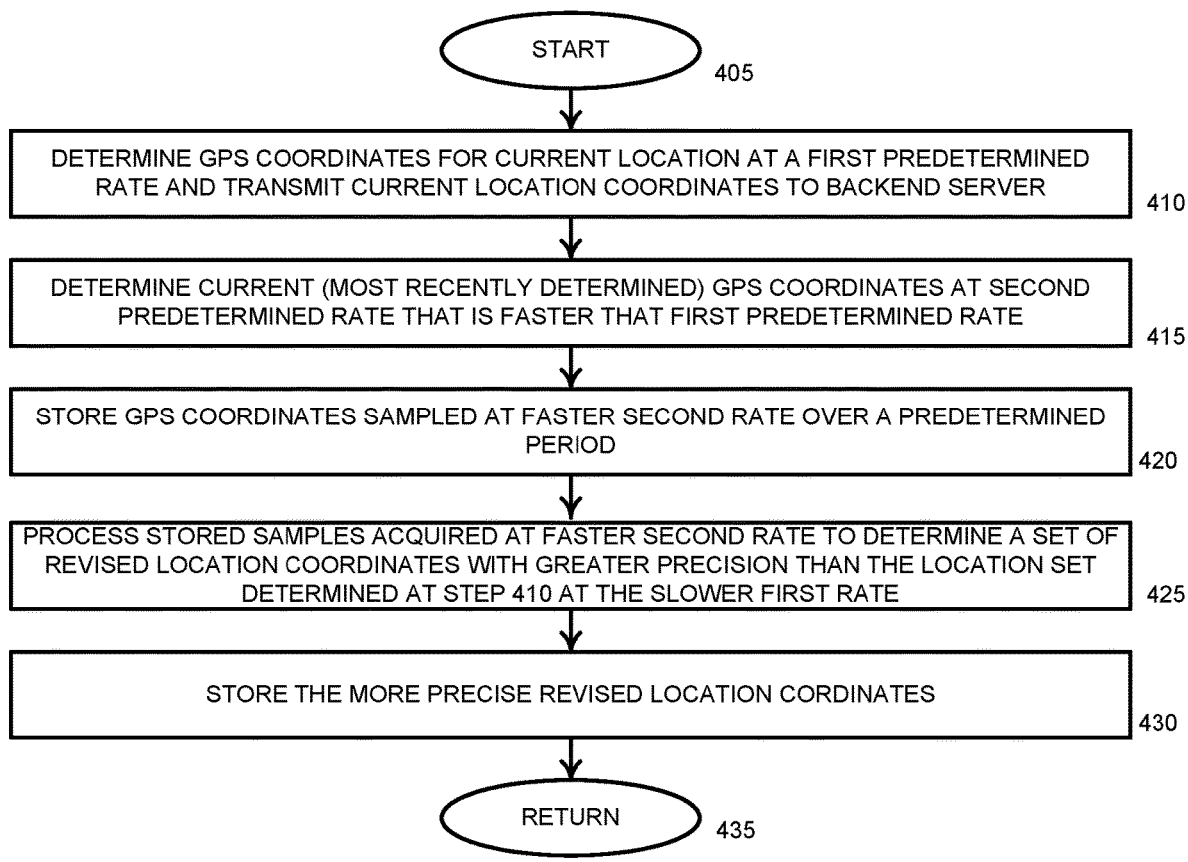
FIG. 4 illustrates a flow diagram of a method for increasing the precision of a set of location coordinates generated by GPS radio circuitry.

Turning now to FIG. 4, the figure illustrates a flow diagram of a method 380 (subroutine 380 shown in FIG. 3.) for increasing the precision of a set of location coordinates generated by GPS radio circuitry. A processor executing method 300, which processor may be running/executing software that instructs the processor to perform the steps of the method by a soil condition detection device 22, or, for one or more steps, backend server 26, as described in reference to FIG. 1, may perform steps to cause a performing of a determination of location information, such as coordinates, to a higher degree of precision than typical GPS receiver circuitry provides. Due to changes in atmospheric conditions, changes in satellite locations above the earth, availability of signals from satellites above the earth, objects in a line-of-sight between a given satellite transmitter in the sky and a GPS receiver in a soil condition detection probe device 22, as well as radio signal noise and interference, a single determination of location information provided by a GPS receiver may not provide an accurate set of location coordinates. In other words, the accuracy of a given single location determination may be accurate within a predetermined tolerance, but that tolerance may be too imprecise for locating a soil condition detection unit 22 that has been buried in the ground on a golf course fairway or green for a number of years. (For example, when the device 22 needs to be replaced because the battery has died.)

According to the United States, "For example, the government commits to broadcasting the GPS signal in space with a global average user range error (URE) of ≤7.8 m (25.6 ft.), with 95% probability. Actual performance exceeds the specification. On May 11, 2016, the global average URE was ≤0.715 m (2.3 ft.), 95% of the time." "[ ] GPS-enabled smartphones are typically accurate to within a 4.9 m (16 ft.) radius under open sky (view source at ion.org). However, their accuracy worsens near buildings, bridges, and trees." https://www.gps.gov/systems/gps/performance/accuracy/, Aug. 25, 2020.

The United States commits to providing satellite signals that a typical user's GPS receiver can process to generate location coordinates within a tolerance of 25.6 feet, and at least on one occasion the global average performance facilitated by GPS satellite signals enabled accuracy within a tolerance, or precision, of 2.3 feet. Although 2.3 feet, and even 16 feet, may be adequate for many location-based applications, such as vehicle movement/tracking/navigation along a roadway, accuracy within a greater precision (i.e., smaller tolerance) when digging up an expensive golf course is desirable.

Returning to discussion of FIG. 4, subroutine method 380 begins in FIG. 4 at step 405 when step 380 is performed in reference to FIG. 3. Continuing with discussion of FIG. 4, at step 410 GPS circuitry that is part of a soil condition detection device transmits GPS signal strings, or 'sentences', at a default rate to a processor of the soil condition detection device. The term 'sentences' is nomenclature used by National Marine Electronics Association ("NMEA"), which provides a data format standard currently used by a majority of location detection devices, including for non-marine uses. (Other data formats that NMEA may be used in aspects described herein.) The default rate may be referred to herein as a first location information transmit, or transmission, rate. At present, a typical location information transmit rate for commercially available GPS circuitry is 1 HZ, or one sentence transmitted to the processor per second. A given GPS receiver may include circuitry that can transmit at a higher rate, such as, for example, 10 Hz. However, since a GPS receiver module often consumes a relatively large amount of power compared to typical long-range wireless module/transceiver/module based on sample/sentence rate, a lower sentence transmit rate is typically desirable for devices that depend on a battery power source. At step 410, GPS circuitry of a soil condition detection unit determines its location at a default rate of typically one sentence per second and transmits the determined location information to a landscape backend server.

At step 415 the soil condition detection device may increase its GPS transmit rate to a second transmit rate that is higher than the default/first transmit rate. For example, the second transmit rate may be 10 Hz, in which case the GPS receiver transmits a location information sentence to the processor of the soil condition detection unit ten times per second. In an aspect, the processor of the soil condition detection unit may acquire and store location information, namely latitude and longitude coordinates, or points, over a predetermined enhanced location determination period. The predetermined enhanced location determination period may be configurable. For example, an installer may enter a period of ten seconds and a predetermined second sentence rate of 10 Hz into a customer application running on a smart phone that then wirelessly communicates values representing the selected sentence rate and the selected predetermined enhanced location determination period to the processor of the soil condition detection unit. The soil condition detection unit would then store location information samples, or sentences, acquired at a sentence rate of ten times per second over the predetermined enhanced location determination period of ten seconds to a memory of the soil condition detection device at step 420. The processor of the soil condition detection device may then calculate revised location information corresponding to the location of the soil condition detection unit based on the samples, or sentences, acquired from the GPS receiver circuitry during the selected/predetermined enhanced location determination period at the selected higher second sample rate, thus providing faster convergence to, or providing more location determination points/samples for better and more accurate convergence to, a centroid according to the mathematical algorithm, which may be a centroid calculation algorithm, performed at step 425.

Alternatively, the installer's customer application may instruct the processor of the soil condition detection unit to acquire GPS location information at the higher second sample rate, or sentence rate, over the selected enhanced location determination period and to transmits information sentence samples acquired during such predetermined period to a services provider's backend server for storage thereon at step 420. The services provider's backend server may then calculate revised location information from all, or part of, the location information sentences received during the enhanced location determination period that were transmitted to the backend server and store such determined revised location information to a table associate such revised location information with the particular solar condition detection unit that the installer is currently installing at step 425. Or, the soil condition detection device may determine at step 425 its revised location information from all, or part of, location information sentences acquired at the higher second sentence rate during the selected/predetermined enhanced location determination period that were stored to a memory of the soil condition detection device at step 420.

A processor of the soil condition detection device, or a processor of the services provider's back end server, may calculate/determine at step 425 revised location information (e.g., latitude and longitude coordinates) corresponding to the soil condition detection device according to a mathematical algorithm, such as, for example, an arithmetic mean of location coordinates corresponding to the sentences acquired at the higher second sentence rate and stored during the predetermined enhanced location determination period. Other algorithms may be used instead, for example a centroid calculated from the location coordinates corresponding to the sentences acquired at the higher second sentence rate and stored during the predetermined enhanced location determination period could be determined. In addition, before performing an arithmetic mean, or a centroid calculation, coordinate sets corresponding to outlier locations could be discarded. The discarding could be performed before or after a first iteration, or pass, of calculating of the arithmetic mean or centroid. For example, a centroid could be calculated from a complete set of all location coordinates corresponding to the sentences acquired at the higher second sentence rate and stored during the predetermined enhanced location determination period, and then outliers from the complete set could be discarded based on predetermined criteria that defines outliers, to result in a refined set of location coordinates for a given soil condition detection device. Both the calculation of a centroid using a set of coordinates acquired during the predetermined enhanced location determination period at the higher second sentence rate, and the discarding of outliers, results in the revised location information corresponding go a given soil condition detection device being accurate to within a much smaller tolerance, (i.e., higher precision) than using a single location coordinate determined at the slower first sentence rate. Furthermore, determining a centroid from sentences sampled at the higher second sentence rate also provides for a faster determination of a revised location information coordinate set for a given soil condition detection device than if the same number of sentences were acquired at the slower first rate during a selected predetermined enhanced location determination period than at the second higher rate. Following the example given above, if the first sentence rate is 1 Hz, the second rate is 10 Hz, and the predetermined enhanced location determination period is 10 seconds, acquiring sentences at a rate of 10 HZ during a period of 10 seconds would result in 100 sentences from which a centroid, or other mathematical result, would be calculated. If 100 sentences were to be determined at the slower sample rate, acquiring 100 samples would take 100 seconds instead of the 10 seconds when the faster second sample rate is used. Continuing with the same example, acquiring 100 sentences at the faster second rate could save an installer 27 minutes for the installation of eighteen soil condition detection devices.

At step 430, the revised location information (e.g., latitude and longitude coordinate set) may be stored in the memory of the soil condition detection device or may be stored in the services provider's backend computer server. The stored revised location information may then be used as the location information corresponding to the soil condition detection device when displaying the location of the device on a map using an interface of the customer application. Thus, the GPS radio circuitry need not regularly wake up and report its location to minimize batter power usage. Subroutine method 380 returns to method 300 shown in FIG. 3 at step 435.

Figure 5:
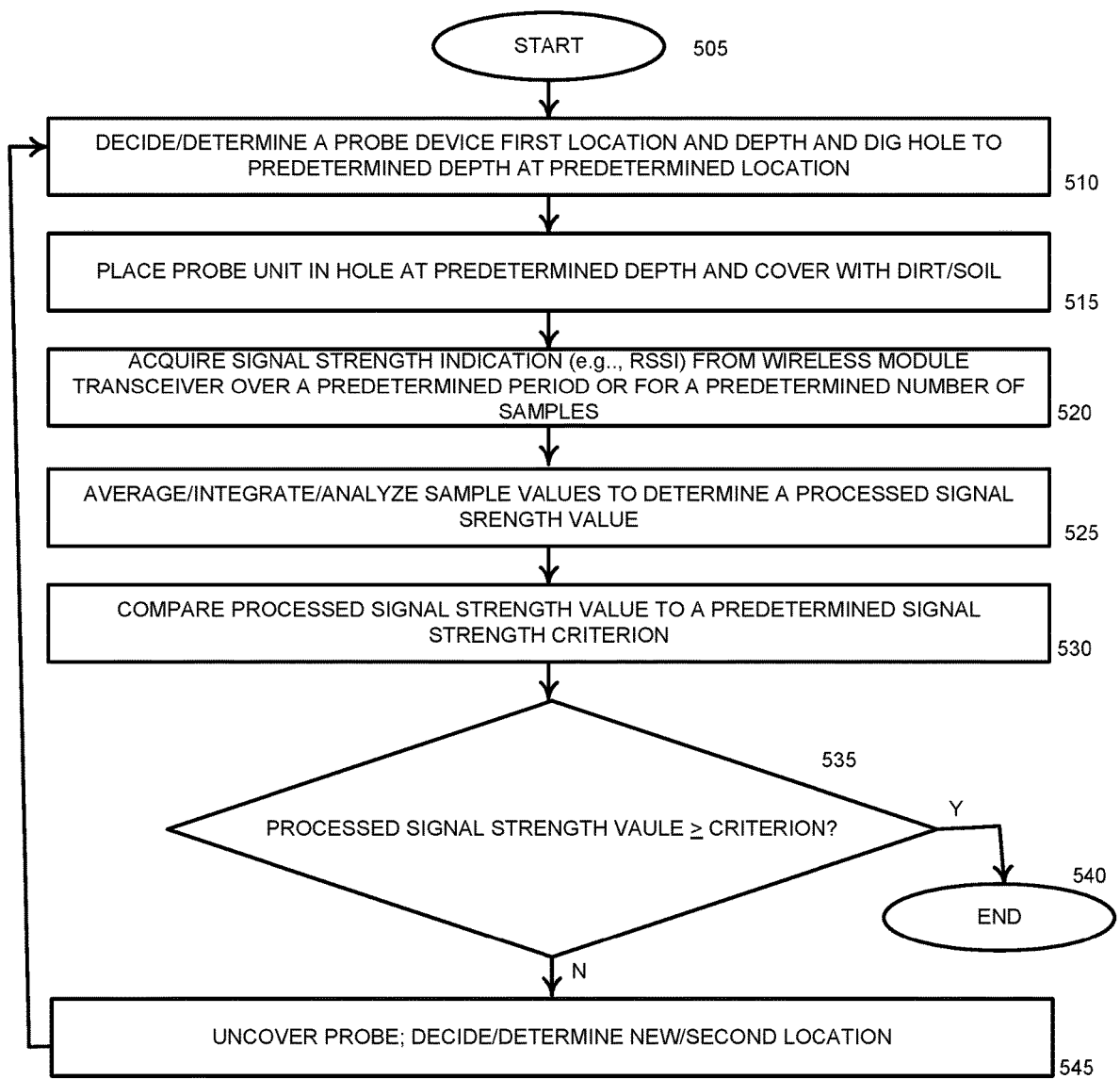
FIG. 5 illustrates a flow diagram of a method for wirelessly determining whether a subterranean location will facilitate adequate wireless transmission and reception of signals to and from a long-range wireless communication network.

Turning now to FIG. 5, the figure illustrates a flow diagram of a method for wirelessly determining whether a subterranean location will facilitate adequate wireless transmission and reception of signals to and from a long-range wireless communication network. A processor executing method 300, which processor may be running/executing software that instructs the processor to perform the steps of the method by a soil condition detection device 22, or, for one or more steps, backend server 26, as described in reference to FIG. 1, may perform the steps to cause a performing of a determination of signal strength at a given location before an installer installs the soil condition detection device at the location. Subroutine method 375 begins in FIG. 5 at step 505.

At step 510 an installer decides on a probe device first location. The installer digs a hole to a predetermined depth. Predetermined depth may be based on the size of the soil condition detection probe device, the type of soil the device is to be buried in, the depth of turf root base, or the location within a landscape. The predetermined depth may be indicated by a visual scale manufactured on the outside of the housing of the soil condition detection device. For example, a probe device may not be buried as deeply in a fairway of a golf course as it is in a putting green of a golf course. Alternatively, a customer application may perform calculations based on the topography of the landscape area, the amount of shade the landscape typically receives, the amount of rainfall, or runoff therefrom that the general location of the landscape receives, the type of soil that makes up the general area where the probe device is to be buried, the external dimensions of the probe device, etc.

At step 515 the installer places the wireless probe unit in the hole that he, or she, dug at its predetermined depth and covers the probe with dirt and/or sod.

In step 520 after having been activated, a subterranean probe device acquires signal strength information relative to signals received from a long-range wireless mobile network during a pre-determined signal strength determination period, or for a predetermined number of signal strength determination samples. The signal strength information may include one or more received signal strength indicator ("RSSI") or Received Channel Power Indicator ("RCPI") measurements. The signal strength measurement information may be transmitted by a long-range wireless transceiver of the probe device to a services provider's back-end computer server for further processing, or a processor on board the wireless probe device may further process the signal strength measurement information.

At step 525, a processor of the subterranean wireless probe, or a processor the service provider's back-end server evaluates the signal strength measurement information. The evaluation may include performing an averaging calculation on the one or more signal strength measurements. The evaluation may include performing an integration of the one or more measurements over the predetermined signal strength determination period, or over a period that corresponds to the predetermined number of signal strength determination samples. The result of the evaluation may be referred to as a processed signal strength value.

At step 530, the processed signal strength value is compared to a predetermined signal strength criterion value, such as a threshold value, to determine whether the location and depth at which the wireless soil condition detection probe is buried is adequate to facilitate wireless communication with radio access network ("RAN") components of a long-range wireless communication network. If a determination is made at step 535 that the processed signal strength value meets the predetermined signal strength criterion value (e.g., the processed signal strength value is equal to or greater than a predetermined signal strength threshold value) subroutine method 375 advances to step 540 and returns to method 300 as shown in FIG. 3.

If, however, a determination is made at step 535 that the processed signal strength value does not meet the predetermined signal strength criterion value (e.g., the processed signal strength value is less than a predetermined signal strength threshold value), a user/customer application instructs at step 545 an installer, on a handheld device, such as a table or smart phone, that he, or she, should bury the wireless probe device at a new second location that is different from the first location. The installer digs up the probe device from the first location and method 380 returns to step 510 with the determination of the new second hole now being referred to as the first hole for iterations of method 375 subsequent to the first iteration thereof. In an aspect, step 515 may be by-passed and signal strength measurement information/values are provided before the burial of the soil condition detection device. If a location of an unburied soil condition detection device is determined during performance of steps 520-545 to be in a "bad coverage" area, an installer/greenskeeper would know not to dig a hole at the predetermined location because burying the unit at the predetermined location would only make coverage worse, and method 500 returns to step 510 for determination of a new location for burial.

As discussed above in reference to FIG. 3B step 373, it will be appreciated that steps 520-545 may be performed multiple times before steps 510-515 are performed to determine that a location will likely provide adequate long-range wireless receive and transmit signal strength when covered in the ground with dirt or grass before a hole is dug to place a unit it. Doing this minimizes the likelihood of digging a hole, placing a unit in the hole, and then covering the unit with dirt only to then discover that the unit cannot transmit or receive long-range wireless signals adequately and thus another hole must be dug in hopes of determining a location that will result in adequate signal strength to or from the long-range wireless transmit/receive module of the probe/unit.

Figure 6:
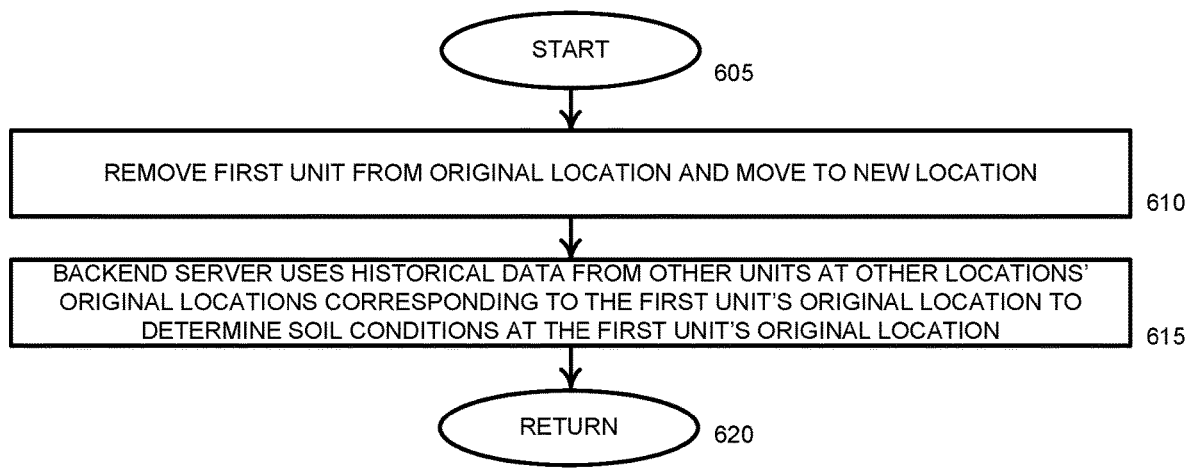
FIG. 6 illustrates a flow diagram of a method for using historical data from a plurality of soil condition detection probe devices to determine soil conditions for a location from which a soil condition detection probe device has been removed.

Turning now to FIG. 6, the figure illustrates a flow diagram of a method 600 for using historical data from a plurality of soil condition detection probe devices to determine soil conditions for a location from which a soil condition detection probe device has been removed. Method 600 starts at step 605. A determination may be made by management personnel of a golf course, by operators of a service provider's back-end server, by a golf course maintenance technician, or by another type of device or individual, to move one wireless soil condition detection device from one location to another after the given device has been in service. Reasons for determining to move a soil condition detection device may include: the device corresponded to a golf course hole (e.g., the $5^{th}$ hole) that may be small and is situated between the $4^{th}$ and $6^{th}$ holes such that information gleaned from soil condition detection devices buried in the ground of these other respective holes provides satisfactory intelligence as to whether to irrigate the $5^{th}$ hole. Or, due to similar shade/sunshine effects on the $5^{th}$ hole as the $4^{th}$ and 6th holes, temperature information from the $4^{th}$ and $6^{th}$ holes provides adequate intelligence as to whether to remove a tarp that covers the $5^{th}$ hole (i.e., if conditions are such that removal of tarps form the $4^{th}$ and $6^{th}$ holes is desirable then tarp removal from the $5^{th}$ hole is deemed desirable too). By removing at step 610 the soil condition probe from the ground so that the probe is no longer used to measure and wirelessly transmit soil condition information corresponding to the $5^{th}$ hole, the probe may be placed elsewhere at the golf course, or other landscape location, to provide more soil condition information relative to the new location.

Because wireless soil condition detection probes wirelessly transmit soil condition information that they detect to a service provider's back-end server for presentation to a customer via the customer's customer application, the probe that was removed at step 610 had been in service at the $5^{th}$ hole along with probes that provide soil condition information relative to the $4^{th}$ and $6^{th}$ holes of the golf course. Therefore, the service provider's back-end server may maintain a database of the customer's historical soil condition information received from all of the wireless probes at the customers location since the probes were placed into service, for example according to method 300 described in reference to FIG. 3. Historical soil condition information relative to the $5^{th}$ hole transmitted by the probe device before it was removed at step 610, and historical soil condition information transmitted from other wireless soil condition detection probes at other holes or locations of the landscape/golf course while the probe that was removed at step 610 was still in service before being removed from the ground at step 610 may be used in an aspect to predict at step 615 the soil conditions for the $5^{th}$ hole even after the removal of the probe at step 610.

Such prediction that may occur at step 615 may include simple correlation and algebra. For example, if the temperature and moisture conditions detected by the probe for the $5^{th}$ hole that was removed at step 610 always were the same as, within a predetermined tolerance, the conditions at the $4^{th}$ or $6^{th}$ holes, or differed from them but always varied in direct proportion to variations at the $4^{th}$ or $6^{th}$ holes, the factor by which the soil conditions at the $5^{th}$ hole differed from those detected by probes at the $4^{th}$ and $6^{th}$ holes could be applied to future condition determinations corresponding to the probes still buried at the $4^{th}$ or $6^{th}$ holes to predict the soil conditions at the $5^{th}$ hole, even after the removal of the $5^{th}$ hole probe at step 610.

In an aspect, a more complex calculation may be used to predict the soil condition that would otherwise be detected by the probe at the $5^{th}$ hole had it not been removed at step 610. Artificial intelligence algorithms may be used to process historical data to determine soil conditions that would have otherwise been detected by the probe that was removed at step 610. For example, if the historical data obtained by the probe for the 5th hole that was removed at step 610 does not always correspond to historical data detected by one or more other probes at the golf course, perhaps because of sunlight/shade being different at different times of the day or year, or because drainage from rain affects the soil near the $5^{th}$ hole differently than other holes, an artificial intelligence algorithm may be used to evaluate the historical data to determine factors, coefficients, and other values to use creating an artificial intelligence learning model that may be refined while before the probe is removed from detecting soil conditions at the $5^{th}$ hole at step 610. Method ends at step 620.

Figure 7:
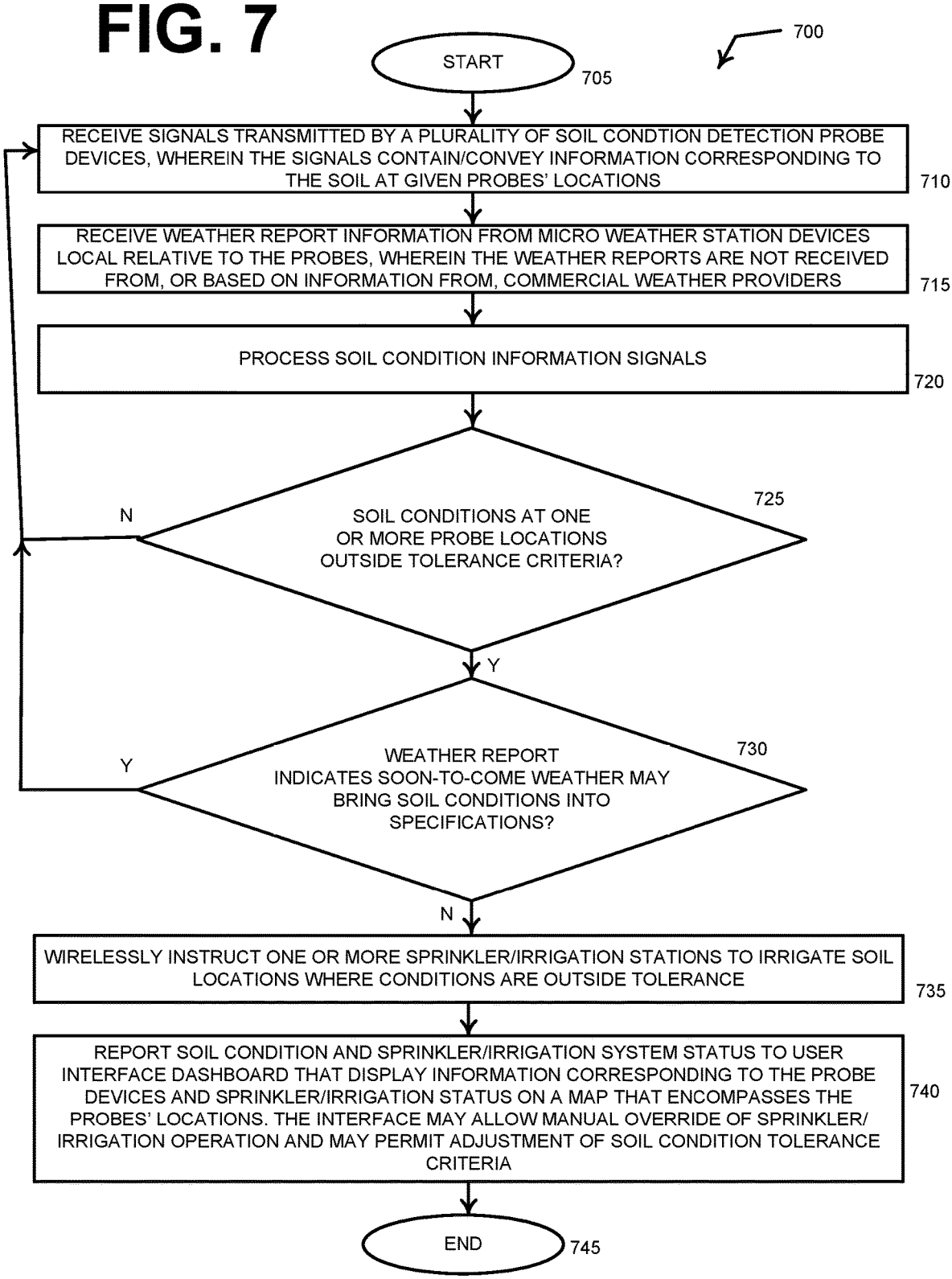
FIG. 7 illustrates a flow diagram of a method for wirelessly managing irrigation and other environmental factors at a landscape using a user interface.

Turning now to FIG. 7, the figure illustrates a flow diagram of a method 700 for wirelessly managing irrigation and other environmental factors at a landscape using a user interface. Method 700 begins at step 705. At step 710 a service provider's back end remote server receives soil condition information wirelessly transmitted by one or more soil condition probe devices wherein signals transmitted by the probe devices contain and convey information corresponding to soil conditions at the location of the one or more probe devices. At step 715 the service provider's backend server receives weather report information from micro weather station devices that are local to the landscape area where the soil condition probe devices are installed. Local weather stations may be installed on poles, on the side of buildings, pedestals on the ground, etc. The local micro weather station(s) provides reports that are not received from commercial weather report providers. Instead, the local micro weather station devices determine local weather based on sensors internal to the local weather stations including, but not limited to, barometers humidity detectors, wind speed detectors, temperature sensors, and the like. At step 720 a service provider's backend server processes the soil condition information received in signals that were wirelessly transmitted by the one or more soil condition detection probe devices. At step 725 a determination is made whether one or more soil conditions detected by the one or more soil condition detection probes is outside a tolerance or criterion/criteria. If none of the conditions reported by the one or more soil condition detection probes is outside the criteria as determined at step 725 method 700 returns to step 710. If however one or more soil conditions is determined at step 725 to be outside a predetermined tolerance or criterion method 700 advances to step 730.

At step 730 a determination is made whether weather report information generated by the micro weather station(s) indicates that soon-to-come weather may bring soil conditions into specifications. For example, if soil condition detection probes indicate that soil conditions are drier than desired but a weather report based on local micro weather stations indicates that rain is imminent, backend server may instruct one or more sprinkler zones or irrigations heads not to operate and not to irrigate the soil that corresponds thereto and method 700 returns step 710.

If, however, a determination is made it step 730 that soon become weather conditions will not bring soil conditions into a specified predetermined criteria or range of values method 700 advances to step 735. At step 735 a service providers backend server sends information that may be wirelessly transmitted to instruct one or more sprinkler stations or irrigation heads at the golf course corresponding to information that indicates that the soil conditions are too dry, to either begin irrigating the golf course or to not alter irrigation according to a predetermined irrigation schedule. The instruction to water or irrigate may include information that establishes a watering/irrigation schedule or updates an existing watering/irrigation schedule. The instruction to water or irrigate may include information that instructs sprinkler zones or irrigation heads to immediately begin watering/irrigating if the sprinkler zones/irrigation heads are not controlled according to a predetermined watering/irrigation schedule.

At step 740, the backed server may report soil conditions or sprinkler/irrigation status to a user interface dashboard of a customer application. The customer application dashboard may be configured to Display devices and irrigation status on a map of the landscape, golf course, agricultural area, etc. The interface dashboard may allow manual override of sprinkler or irrigation operation and may permit adjustment of soil condition criteria that may be used at step 725 to determine whether soil conditions reported by the one or more soil condition detection probes are outside of predetermined criteria. Method 700 ends at step 745.

Figure 8:
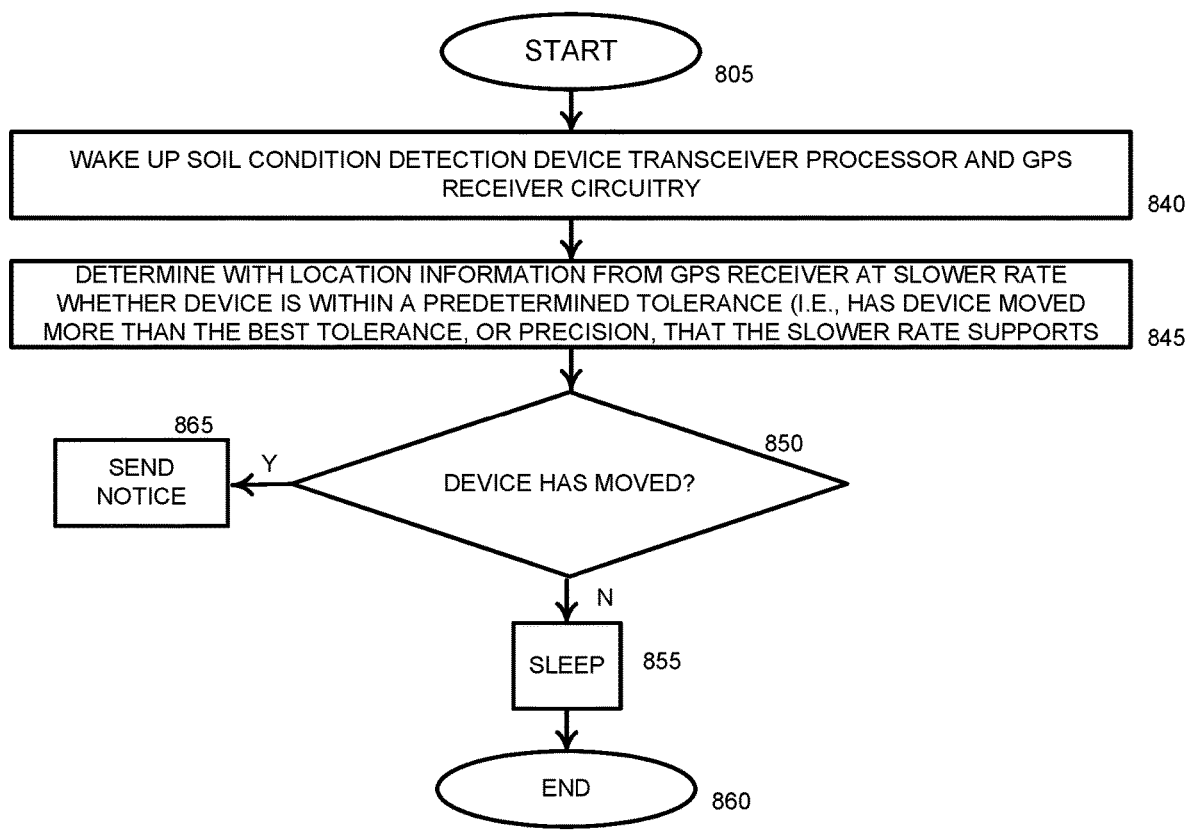
FIG. 8 illustrates a flow diagram of a method for wirelessly determining whether a soil condition detection device has moved, which determining may be triggered from detection of acceleration by one or more accelerometers in a soil condition detection device.

Turning now to FIG. 8, the figure illustrates a flow diagram of a method 800 for wirelessly determining whether a soil condition detection device has moved. Method 800 begins at step 805. In an aspect, after a given soil condition detection device has been installed, the GPS circuitry of the soil condition detection device may wake up according to a predetermined GPS wake-up command, wake schedule, or wake instruction, at step 840. Or, a user of the user/customer application may use an interface thereof to instruct the processor of the soil condition detection device to instruct the GPS receiver to wake up and report its location, preferably using the slower default first sentence rate—only a GPS fix/lock and a single coordinate location may be needed—to determine whether the soil condition detection device has been moved. Alternatively, upon detection by an accelerometer at step 840 of acceleration above a predetermined GPS wake-up threshold, the accelerometer of the soil condition detection device may trigger the GPS circuitry of the device to wake up and determine coordinates corresponding to its location, and cause the transceiver processor/module of the device to report said location coordinates to the services provider's back end server upon detection of movement of the device and the triggering of the device wake-up based thereon.

After waking up, a determination of a given soil condition detection device's current after-installation location is made at step 845, preferably by acquiring location information sentences at a first/default sentence rate. A comparison is made at step 850 between the current after-installation location and the revised location information obtained at a second sentence rate that is higher than the first/default sentence rate as described in reference to subroutine method 375 shown in FIG. 4. If a determination is made as a result of the comparison at step 850, either by the processor of the soil condition detection device or a service's provider's backend server, that the given soil condition detection device has not moved the GPS radio circuitry of the soil condition detection device goes to sleep at step 855 and method 800 ends at step 860. If a determination is made at step 850 that the soil condition detection device has moved relative to the location that was stored at step 430 as described in reference to FIG. 4, an alert is sent at step 865 to a service provider's backend server or to a user/customer application notifying that the device has been moved. The GPS radio circuitry of the soil condition detection device then goes to sleep at step 855 and method 800 ends at step 860.

Figure 10:
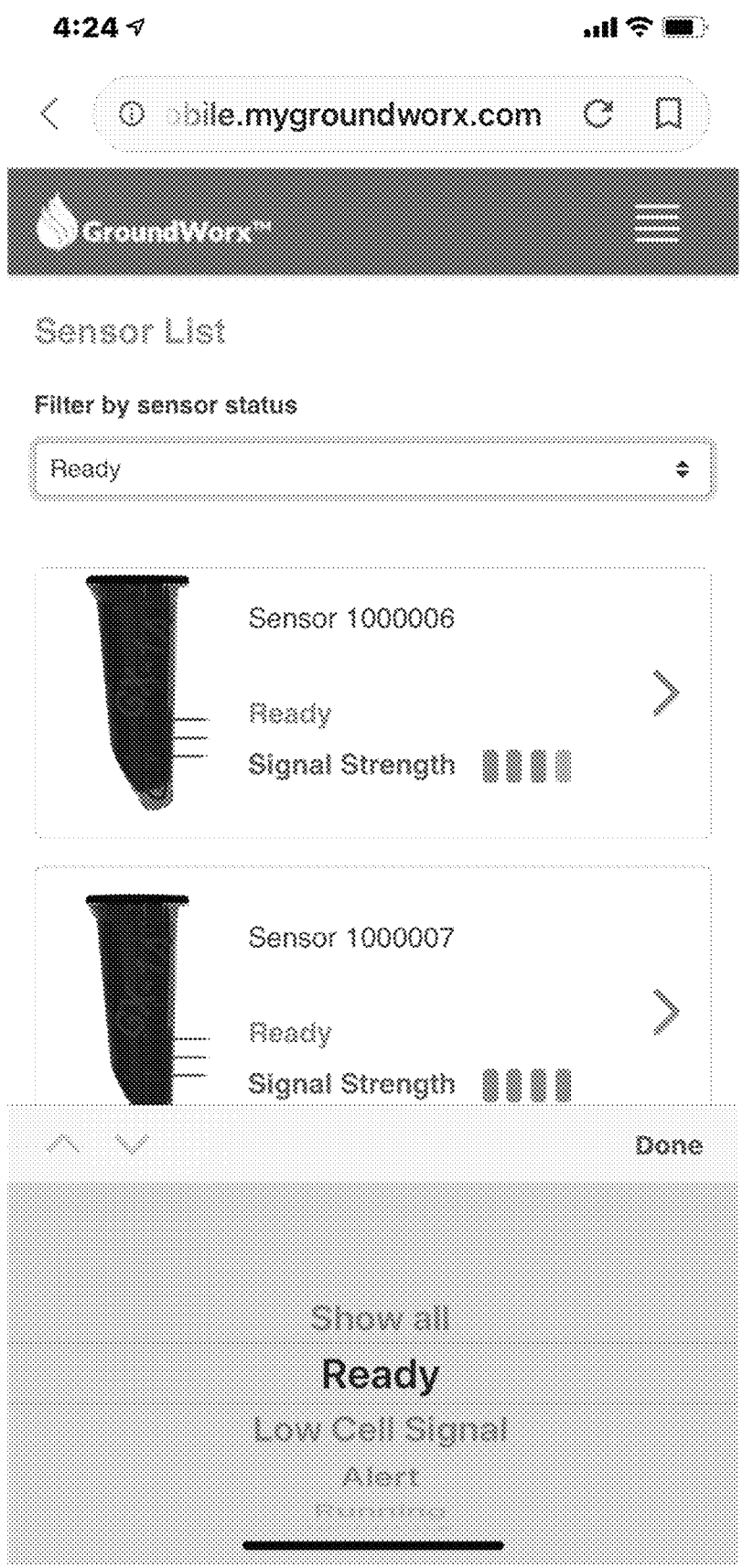
Figure 11:
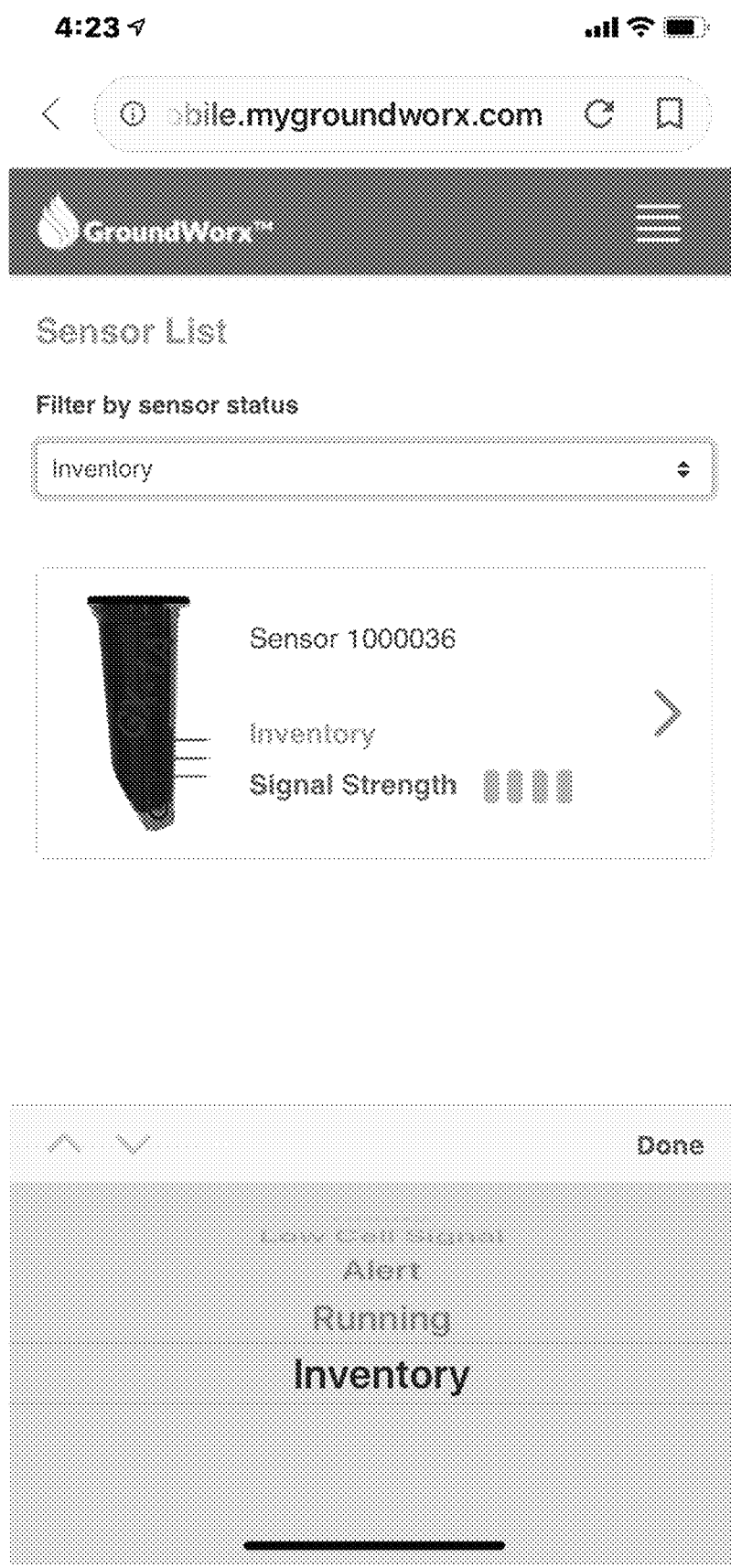
Figure 12:
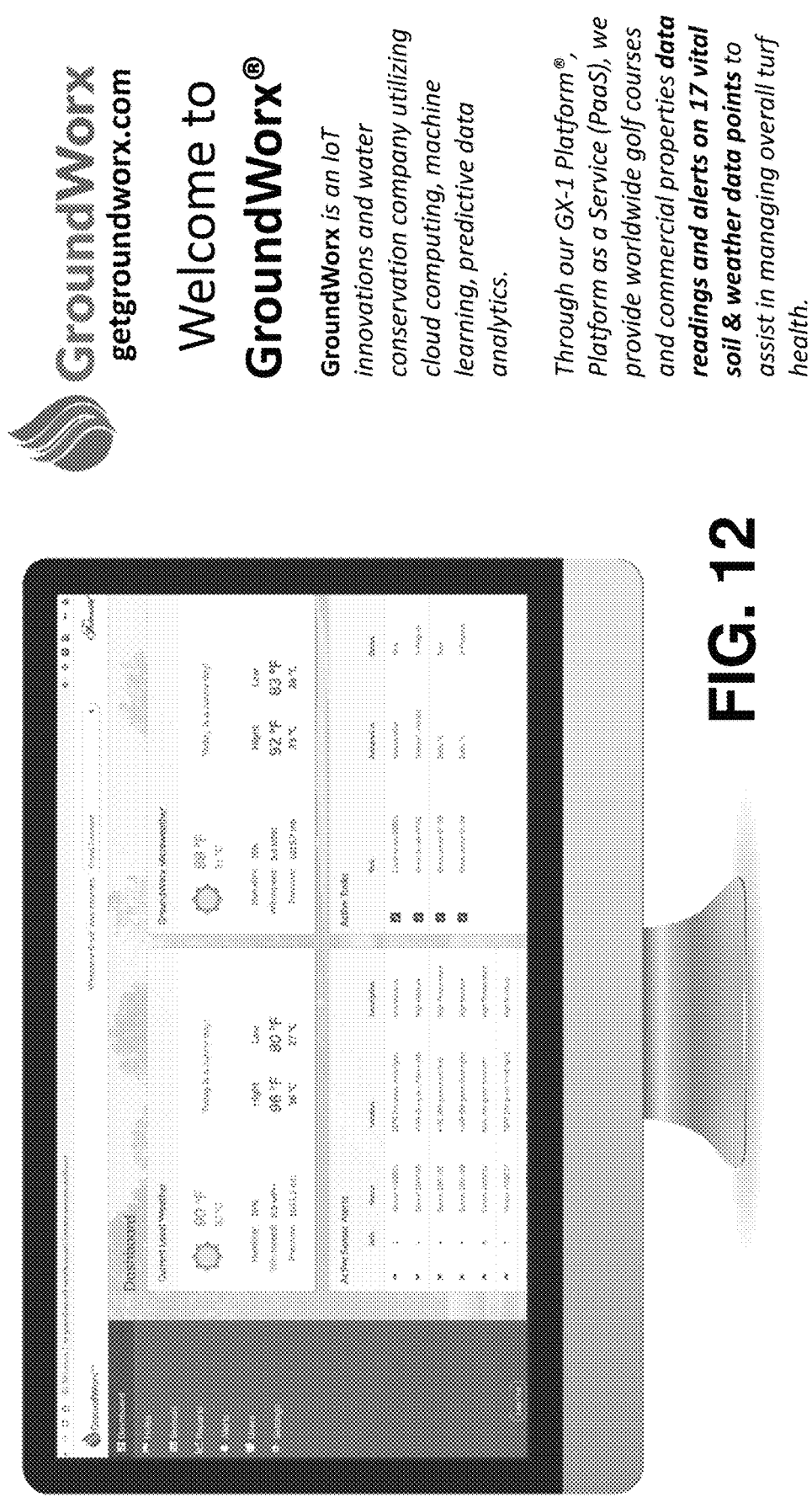
FIG. 12 illustrates a view of a Platform as a Service ("Paas") customer application user interface dashboard the shows the pertinent information relative to a monitored area of land.
Figure 13:
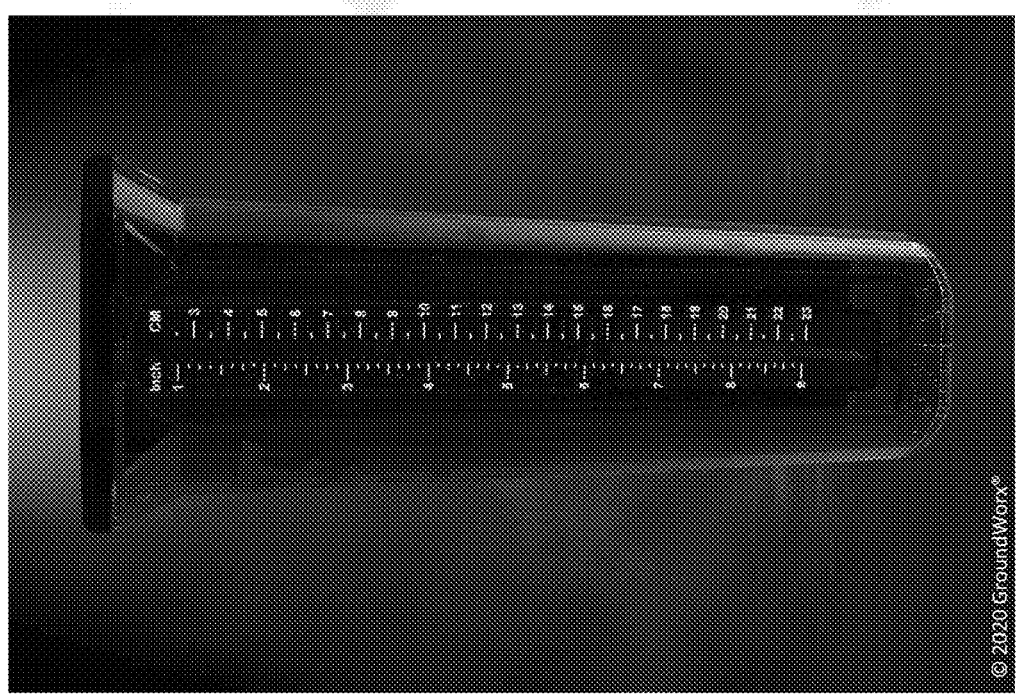
FIG. 13 illustrates a side view of an outside housing of a soil condition detection device.
Figure 14:
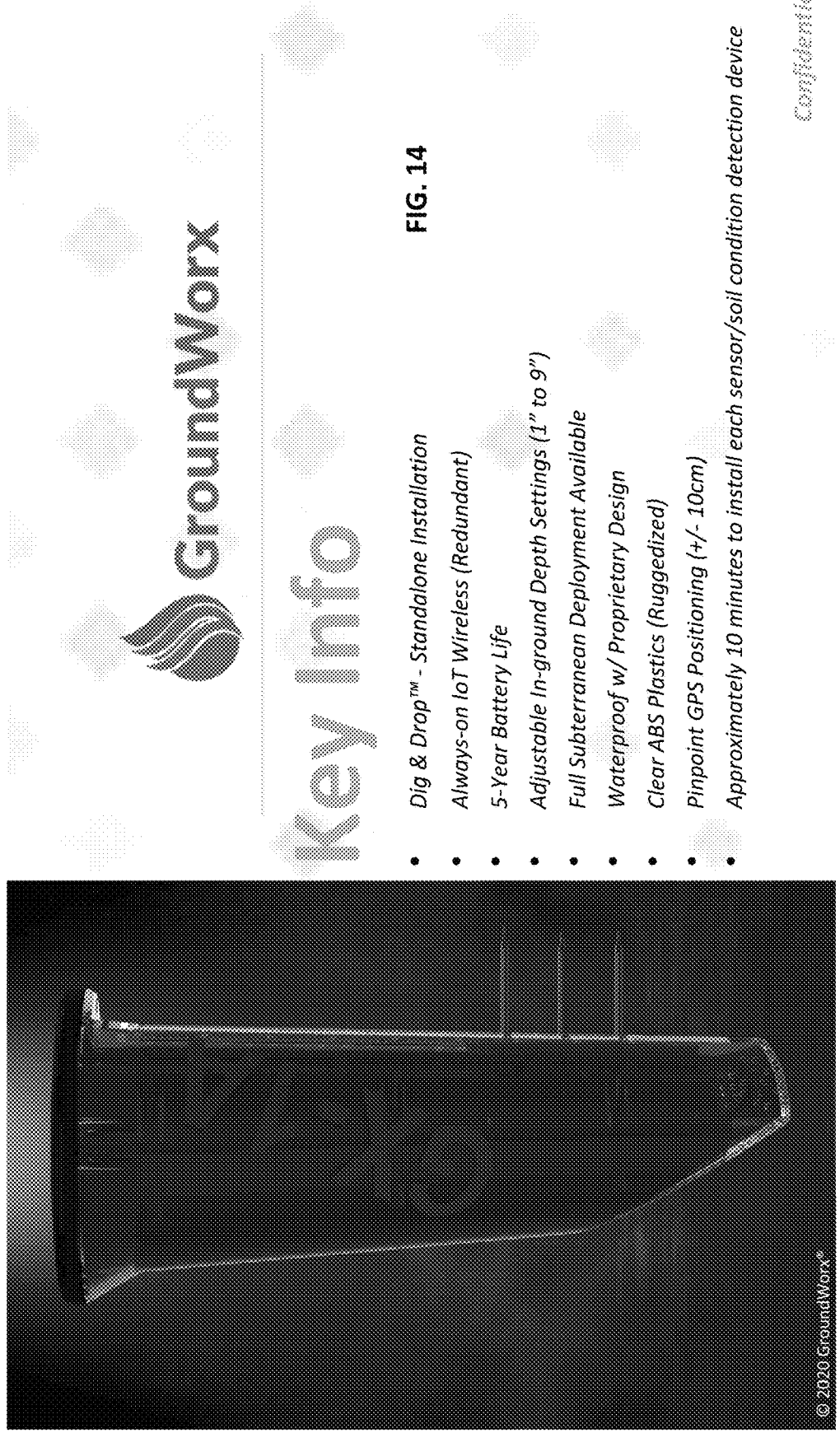
FIG. 14 illustrates a different side view of an outside housing of a soil condition detection device showing soil condition parameter detection sensor probes that project from through the housing.

FIGS. 9, 10, and 11 illustrate an installer interface of a customer application that indicates a predetermined depth to bury a soil condition detection probe device based on signal strength as a desired location to place a subterranean probe device. The customer application determines signal strength at the probe device based on signal strength measurements in a manner similar to the method described in reference to FIG. 4. The probe device acquires multiple samples of signal strength and averages, integrates, or otherwise mathematically processes the sampled data to determine processed sample data value. The probe device transmits the processed sample data value to the services provider's backend server, which determines a depth at which the probe may be buried and still likely have adequate long-range wireless service as shown in FIG. 9.

In an aspect, the installer interface has a filter set to display all probe devices that are 'READY' to be deployed as shown in FIG. 10.

In an aspect, the installer interface has a filter set to display all probe devices that are in 'INVENTORY' that have not been activated yet as shown in FIG. 11.

What is claimed is:
1. A method for installing a wireless soil condition detection device in a subterranean location, comprising:
activating a wireless transceiver of the soil condition detection device that includes a processor to:
receive signals from one or more soil condition parameter detection sensors;
cause the transceiver to wirelessly transmit and receive information corresponding to the signals received from the one or more soil condition parameter detection sensor; and
wherein the transceiver is configured to communicate wirelessly with a long-range wireless communication network;
at a first subterranean location monitoring at one or more points in time the strength of wireless radio signals received by the transceiver from the long-range wireless communication network;
processing over a predetermined period, or for a predetermined number of samples, the values corresponding to the strength of wireless radio signals received by the transceiver from the long-range wireless communication network to determine a processed received signal strength;

comparing the processed received signal strength to a predetermined signal strength criterion;
determining whether the processed received signal strength meets the predetermined signal strength criterion, and
alerting an installer whether or not to install the soil condition monitor device at the first subterranean location based on the comparing of the processed received signal strength to the predetermined signal strength criterion.

2. The method of claim 1 wherein the activating of the wireless transceiver includes causing switch contacts of a switch having a component external to the soil condition monitoring device to complete a circuit to thereby provide electrical power to the transceiver.

3. The method of claim 2 wherein the switch having a component external to the soil condition detection device is a reed switch; wherein the component external to the soil condition detection device is magnetic, wherein the component external to the soil condition detection device is temporarily held in a position such that the contacts do not provide a completed circuit to provide power to the transceiver, and wherein the causing of the switch contacts to complete the circuit to thereby provide electrical power to the transceiver includes removing an adhesive-coated tape such that a bias of the component external to the device moves the component in a direction of at least one of the contacts.

4. The method of claim 1 wherein the predetermined signal strength criterion is based on a signal strength attenuation value that corresponds to a type of soil that will cover the soil condition detection device at the first subterranean location.

5. The method of claim 1 further wherein the installer is alerted not to install the soil condition detection device at the first subterranean location if the processed received signal strength does not meet the predetermined signal strength criterion.

6. The method of claim 1 wherein the predetermined signal strength criterion is based on a signal strength attenuation value that corresponds to a type of soil that will cover the soil condition detection device at the first subterranean location and on a predetermined depth at which the device is to be buried.

7. The method of claim 5 wherein the steps of claim A are performed for a second subterranean location when the processed received signal strength for the first subterranean location does not meet the predetermined signal strength criterion.

8. A method for refining the precision of the determining of location information of a soil condition detection device provided by a multi-station wireless location system, comprising:
capturing first location information based on transmission signals from the multi-station wireless location system at the first location at a first sample rate;
determining that the soil condition detection device has not moved from the first location during a predetermined first period;
storing location information corresponding to a sample captured at the first sample rate as indicating the location of the soil condition monitor device;
capturing location information based on transmission signals from the multi-station wireless location system at a second sample rate at the first location for a second plurality of samples during a predetermined second period;
determining a centroid of data points corresponding to the second plurality of samples captured while the soil condition monitor device is at the first location;
replacing the information corresponding to the sample captured at the first sample rate with the centroid corresponding to the second plurality of samples as indicating the location of the soil condition monitor device; and
wherein the second sample rate is higher than the first sample rate.

9. The method of claim 8 wherein the multi-station wireless location system is a Global Positioning Satellite system.

10. The method of claim 8 further comprising:
determining, after the replacing of the information corresponding to the sample captured at the first sample rate with the centroid corresponding to the second plurality of samples as indicating the location of the soil condition monitor device, second location information corresponding to the location of the soil condition monitor device at the first sample rate;
determining that the soil condition detection device has been moved from the first location based on a comparison between the centroid corresponding to the second plurality of samples and the second location information; and
notifying a service provider's backend server that the soil condition monitor device has moved from the first location when the comparison between the centroid and the second location information indicates a difference that is greater than a predetermined location difference value.

11. The method of claim 10 wherein the predetermined location difference value is based on the precision in determining location information that is obtainable from signals of the multi-station wireless location system sampled at the first sample rate.

12. The method of claim and 8 wherein the sample rates are sentence rates.

13. A method, comprising:
receiving soil condition information transmitted wirelessly from each of a plurality of subterranean soil condition detection devices buried at corresponding original locations within an area of land during a first period;
storing the soil condition information corresponding to each of the plurality of subterranean soil condition detection devices received during the first period in a customer location table;
identifying one of the plurality of subterranean soil condition detection devices to be moved from its corresponding original location;
moving the identified one of the plurality of subterranean soil condition detection devices from its corresponding original location to a new location within the area of land;
during a second period, receiving soil condition information transmitted wirelessly from each of the plurality of subterranean soil condition detection devices buried at corresponding locations within an area of land, including the identified one of the plurality of subterranean soil condition detection devices being buried at its new location within the area of land; and
determining the soil condition at the original location of the identified one of the plurality of subterranean soil condition detection devices that was moved from its original location to its new location based on soil condition information received during the first period from at least one of the plurality of subterranean soil condition detection devices other than the identified subterranean soil condition detection device that was moved and based on soil condition information received during the second period from the at least one of the plurality of subterranean soil condition detection devices other than the identified subterranean soil condition detection device that was moved.

14. The method of claim 13 wherein the determining of the soil condition at the original location of the identified one of the plurality of subterranean soil condition detection devices that was moved from its original location to its new location includes processing with an artificial intelligence algorithm the soil condition information corresponding to each of the plurality of subterranean soil condition detection devices received during the first period to determine an original location model corresponding to the location of the soil condition detection device that was moved, and applying the original location model to the soil condition information transmitted wirelessly from each of the plurality of subterranean soil condition detection devices during the second period, except for the device that was moved to a new location, to estimate the soil conditions at the original location of the device that was moved during the second period.

15. The method of claim 14 wherein the original location model is determined using a supervised regression algorithm.

16. The method of claim 13 wherein the determining of the soil condition at the original location of the identified one of the plurality of subterranean soil condition detection devices that was moved from its original location to its new location includes processing with a neural network the soil condition information corresponding to each of the plurality of subterranean soil condition detection devices received during the first period to determine an original location model corresponding to the location of the soil condition detection device that was moved, and applying the original location model to the soil condition information transmitted wirelessly from each of the plurality of subterranean soil condition detection devices during the second period, except for the device that was moved to a new location, to estimate the soil conditions at the original location of the device that was moved during the second period.

* * * * *